US008298136B2

(12) United States Patent  
Kimura et al.

(10) Patent No.: US 8,298,136 B2  
(45) Date of Patent: Oct. 30, 2012

(54) IN-VIVO EXAMINATION SYSTEM

(75) Inventors: Atsushi Kimura, Akiruno (JP); Hironobu Takizawa, Hino (JP); Ryoji Sato, Fuchu (JP)

(73) Assignee: Olympus Medical Systems Corp., Tokyo (JP)

( * ) Notice: Subject to any disclaimer, the term of this patent is extended or adjusted under 35 U.S.C. 154(b) by 191 days.

(21) Appl. No.: 12/907,280

(22) Filed: Oct. 19, 2010

(65) Prior Publication Data

US 2011/0224490 A1  Sep. 15, 2011

Related U.S. Application Data

(63) Continuation of application No. PCT/JP2010/050352, filed on Jan. 14, 2010.

(30) Foreign Application Priority Data

Apr. 20, 2009  (JP) ................................ 2009-102291

(51) Int. Cl.  
*A61B 1/04* (2006.01)

(52) U.S. Cl. ....................................... 600/117; 600/118

(58) Field of Classification Search .................. 600/109, 600/117, 118, 160  
See application file for complete search history.

(56) References Cited

U.S. PATENT DOCUMENTS

| | | | |
|---|---|---|---|
| 2004/0225223 A1* | 11/2004 | Honda et al. .................. | 600/476 |
| 2004/0249291 A1* | 12/2004 | Honda et al. .................. | 600/476 |
| 2006/0203089 A1* | 9/2006 | Akimoto et al. .............. | 348/113 |
| 2007/0055128 A1* | 3/2007 | Glossop ........................ | 600/407 |
| 2008/0292150 A1* | 11/2008 | Hirakawa ...................... | 382/128 |
| 2009/0003732 A1* | 1/2009 | Oda .............................. | 382/305 |

FOREIGN PATENT DOCUMENTS

| | | |
|---|---|---|
| JP | 06-304127 A | 11/1994 |
| JP | 2001-179700 | 7/2001 |
| JP | 2002-200030 | 7/2002 |
| JP | 2003-225195 A | 8/2003 |
| JP | 2003-524448 A | 8/2003 |
| JP | 3898781 | 1/2007 |
| JP | 2007-307396 A | 11/2007 |
| JP | 2007-330348 | 12/2007 |
| JP | 2008-504860 A | 2/2008 |
| JP | 2008-100075 A | 5/2008 |
| JP | 2009-61013 A | 3/2009 |

(Continued)

OTHER PUBLICATIONS

Decision of a Patent Grant for Application No. 2010-540973 dated Aug. 2, 2011 together with English language translation.

(Continued)

*Primary Examiner* — John P Leubecker  
(74) *Attorney, Agent, or Firm* — Scully, Scott, Murphy & Presser, P.C.

(57) ABSTRACT

An in-vivo examination system includes a body-insertable apparatus that moves in a subject; and an external device that acquires information about an inside of the subject. The external device includes a location acquiring unit that acquires a plurality of first locations of the body-insertable apparatus in the subject; a trajectory generating unit that generates a first movement trajectory of the body-insertable apparatus in the subject, based on the plurality of first locations; a trajectory storage unit that stores a second movement trajectory; and a scale adjusting unit that adjusts the first movement trajectory to the second movement trajectory.

1 Claim, 17 Drawing Sheets

FOREIGN PATENT DOCUMENTS

| | | |
|---|---|---|
| JP | 2009-509621 | 3/2009 |
| WO | WO 2005/053518 A1 | 6/2005 |
| WO | WO 2007/036941 A2 | 4/2007 |
| WO | WO 2007/123130 A1 | 11/2007 |
| WO | WO 2008/099851 A1 | 8/2008 |

OTHER PUBLICATIONS

International Search Report dated Apr. 13, 2010 issued in PCT/JP2010/050352.

English abstract only of International Publication No. WO 00/22975, (Apr. 27, 2000).

English abstract only of International Publication No. WO 2006/003652 A2, (Jan. 12, 2006).

English abstract only of Japanese Patent Application Publication No. JP 10-020214, (Jan. 23, 1998).

Japanese Office Action No. 877067, dated Dec. 7, 2010, issued in 2010-540973, together with English language translation.

Japanese Office Action dated Apr. 12, 2011 together with an English language translation.

* cited by examiner

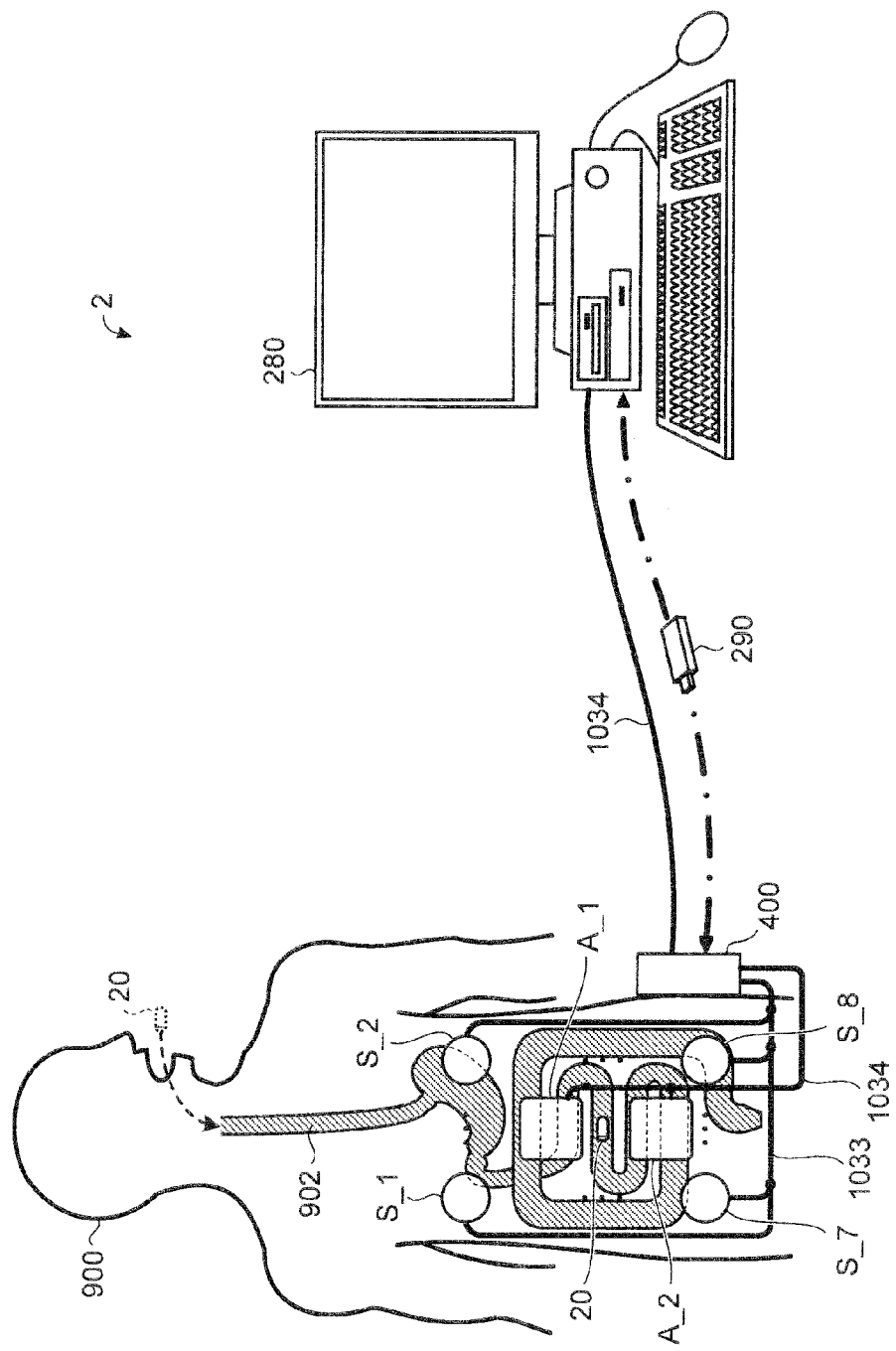

ical significance of this invention will be better understood by reading the following detailed description of presently preferred embodiments of the invention, when considered in connection with the accompanying drawings.
IN-VIVO EXAMINATION SYSTEM

CROSS-REFERENCE TO RELATED APPLICATIONS

This application is a continuation of PCT international application Ser. No. PCT/JP2010/050352 filed on Jan. 14, 2010 which designates the United States, incorporated herein by reference, and which claims the benefit of priority from Japanese Patent Applications No. 2009-102291, filed on Apr. 20, 2009, incorporated herein by reference.

BACKGROUND OF THE INVENTION

1. Field of the Invention

The present invention relates to an in-vivo examination system, and more particularly, to an in-vivo examination system for examining a subject such as a person or an animal.

2. Description of the Related Art

Examples of conventional devices for observing the inside of a subject such as a person or an animal include an endoscope that has two end portions, with one of the end portions being inserted into a subject to observe the inside of the subject (hereinafter referred to simply as an endoscope), and a capsule-type endoscope (hereinafter referred to simply as a capsule endoscope). Examples of endoscopes include an electronic endoscope that has a CCD (Charge Coupled Device) sensor provided in its end portion, and a fiberscope that has a bundle of optical fibers inserted into a tubular probe. Such a probe is inserted into a subject from the mouth or anus of the subject, and captures images of the inside of the subject (see Japanese Patent Publication No. 3,898,781, for example). On the other hand, a capsule-type medical device has such a size as to be swallowed by a person or an animal. A capsule-type medical device is inserted orally into a subject, and captures images of the inside of the subject on a regular basis. The captured images of the inside of the subject are transmitted as radio signals to an external receiving device. An observer reproduces a plurality of images obtained by an endoscope or a capsule endoscope on a display device individually or sequentially, and observes the images so as to examine the inside of the subject.

In recent years, there has been a suggested technique by which the current location of the end portion of the probe of an endoscope is detected, and the detected current location is incorporated into a subject's internal three-dimensional image generated beforehand with the use of another modality. The three-dimensional image thereof is then displayed (see Japanese Laid-open Patent Publication No. 2002-200030, for example). By this conventional technique, while viewing a three-dimensional image as a virtual space that reproduces the inside of a subject, an operator can handle the end portion of the probe of an endoscope in the real space, and guide the end portion of the probe to a desired location. Accordingly, the end portion of the probe can be guided to the desired location more accurately and quickly.

SUMMARY OF THE INVENTION

An in-vivo examination system according to an aspect of the present invention includes a body-insertable apparatus that moves in a subject; and an external device that acquires information about an inside of the subject. The external device includes a location acquiring unit that acquires a plurality of first locations of the body-insertable apparatus in the subject; a trajectory generating unit that generates a first movement trajectory of the body-insertable apparatus in the subject, based on the plurality of first locations; a trajectory storage unit that stores a second movement trajectory; and a scale adjusting unit that adjusts the first movement trajectory to the second movement trajectory.

An in-vivo examination system according to another aspect of the present invention includes a body-insertable apparatus that moves in a subject; and an external device that acquires information about an inside of the subject. The external device includes a location acquiring means for acquiring a plurality of first locations of the body-insertable apparatus in the subject; a trajectory generating means for generating a first movement trajectory of the body-insertable apparatus in the subject, based on the plurality of first locations; a trajectory storage means for storing a second movement trajectory; and a scale adjusting means for adjusting the first movement trajectory to the second movement trajectory.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 12 is a schematic view showing an example structure of an endoscope system according to a second embodiment;

DETAILED DESCRIPTION OF THE PREFERRED EMBODIMENTS

Exemplary embodiments for carrying out the invention will be explained in detail below with reference to the accompanying drawings. In the following description, the respective embodiments schematically show the shapes, sizes, and positional relationships merely in such a manner that the contents of the present invention can be understood, and therefore, the present invention is not limited to the shapes, sizes, and positional relationships illustrated in the respective drawings.

First Embodiment

In the following, the structure and operations of a first embodiment of the present invention are described in detail, with reference to the drawings. In the first embodiment, an endoscope system 1 as an in-vivo examination system using an endoscope 100 as an in-vivo device is described as an example. In the first embodiment, a so-called electronic endoscope that has an imaging device such as a CCD (Charge-Coupled Device) array provided in a end portion 102 is described as an example of the endoscope 100. However, the present invention is not limited to that, and may be applied to various tubular endoscopes such as so-called fiberscopes.

Figure 1:
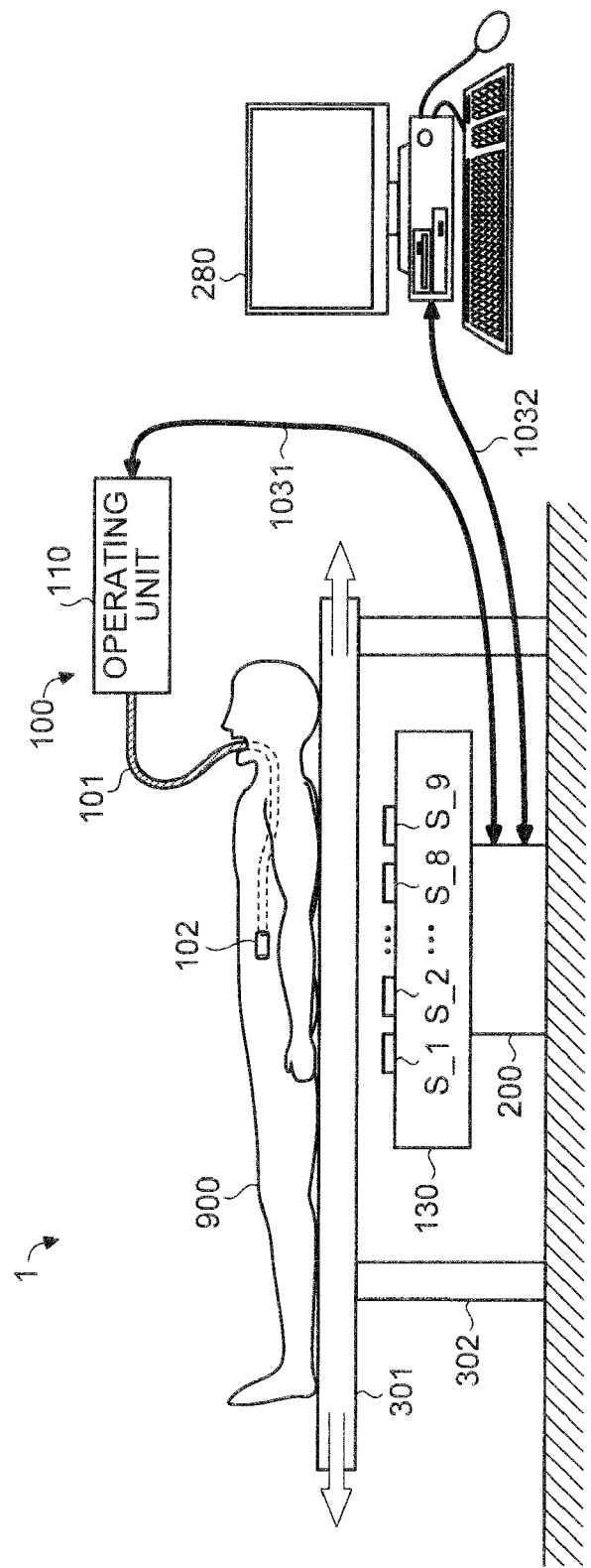
FIG. 1 is a schematic view showing an example structure of an endoscope system according to a first embodiment.
Figure 2:
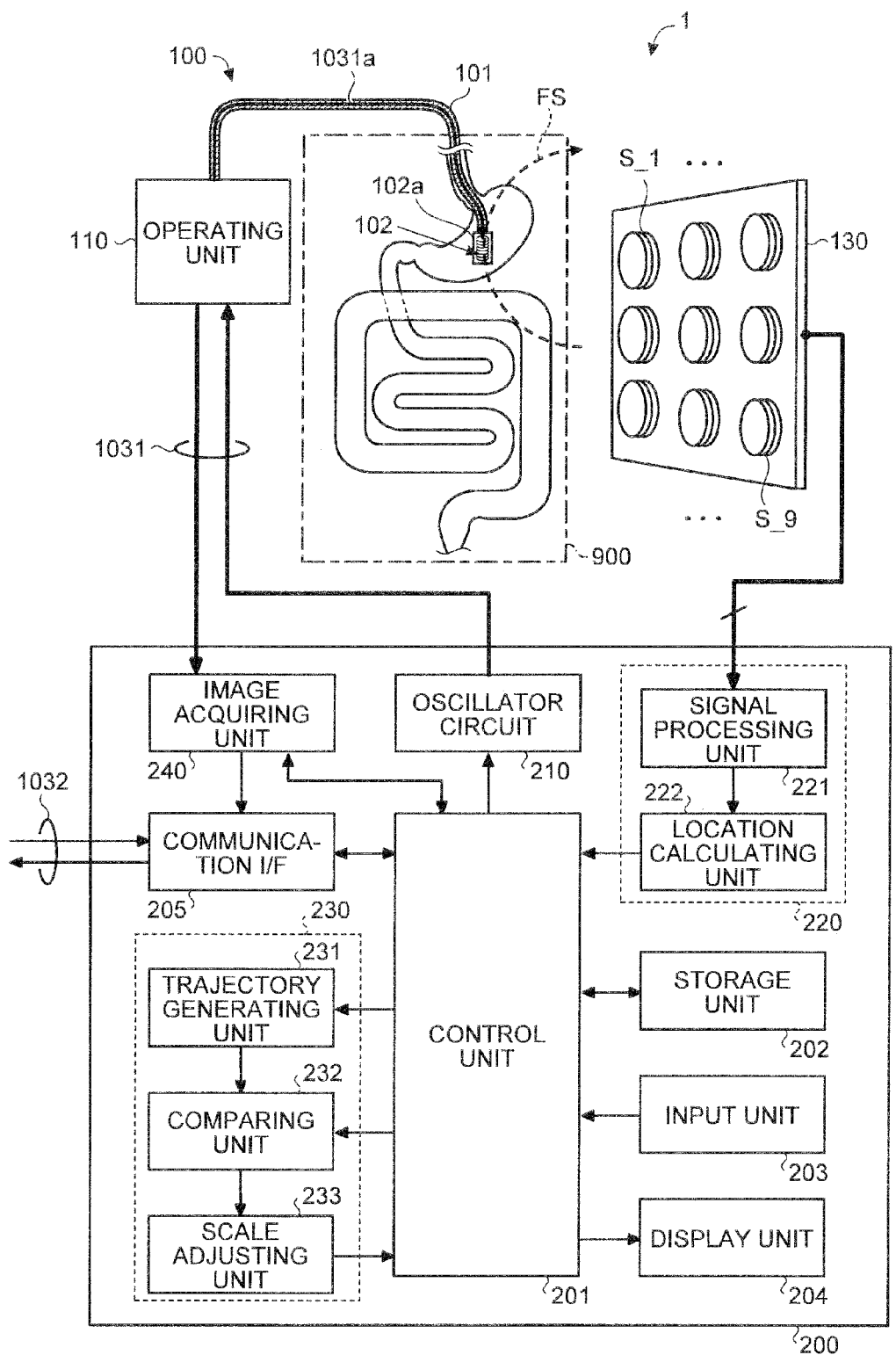
FIG. 2 is a block diagram showing more specific example structures of an endoscope and a receiving device in the endoscope system according to the first embodiment.

FIG. 1 is a schematic view of an outline of an example structure of the endoscope system 1 according to the first embodiment. FIG. 2 is a block diagram showing more specific example structures of the endoscope 100 and a receiving device 200 in the endoscope system 1 according to the first embodiment.

As shown in FIG. 1, the endoscope system 1 includes: the endoscope 100 that has a probe 101 inserted from the end portion 102 into a subject 900, and an operating unit 110 that operates the probe 101; one or more sense coils S_1 through S_9 (hereinafter arbitrary sense coils will be denoted by S); a fixing plate 130 that fixes the sense coils S; the receiving device 200 connected to the endoscope 100 via cables 1031; a display device 280 connected to the receiving device 200 via cables 1032; a bed 301 on which the subject 900 is placed; and a movable table 302 that supports the bed 301 so as to be able to move horizontally with respect to the sense coils S. The display device 280 may be an information processing apparatus such as a personal computer or a workstation, or a display such as a liquid crystal display or an organic EL display. In this structure, the receiving device 200 and the display device 280 are so-called external devices. Accordingly, the receiving device 200 and the display device 280 may be formed with the use of a single information processing apparatus.

As shown in FIG. 2, the receiving device 200 includes: an oscillator circuit 210 that oscillates to output a sinusoidal signal at a predetermined frequency to the cables 1031; a location acquiring unit 220 that acquires the location and orientation of the end portion 102 of the probe 101; a trajectory acquiring unit 230 that generates information about the movement trajectory of the end portion 102, using the location information contained in the acquired information about the location and orientation; an image acquiring unit 240 that receives image data that is obtained by the endoscope 100 through the operating unit 110; a control unit 201 that controls the inside of the receiving device 200; a storage unit 202 that holds various kinds of programs and various kinds of data as needed; an input unit 203 to which an operator inputs various settings, instructions, and the like of the receiving device 200; a display unit 204 that displays various kinds of information such as setting information; and a communication interface (I/F) 205 that exchanges various kinds of data with the display device 280 via the cables 1032.

The sinusoidal signal output to the cables 1031 is input to the operating unit 110 of the endoscope 100, and is then input from the operating unit 110 to a source coil 102a that is mounted in the end portion 102 via a signal line 1031a buried in the probe 101. With this arrangement, an alternating current at a predetermined frequency flows in the source coil 102a in the end portion 102, and a magnetic field FS at a predetermined frequency is output to the surrounding area. The oscillation at the oscillator circuit 210 is controlled by the control unit 201, for example.

The magnetic field FS generated by the source coil 102a is sensed as a voltage change by the sense coils S. That is, in each of the sense coils S, voltage changes are caused in accordance with the portions of the magnetic field at the respective locations. In the first embodiment, the nine sense coils S, which are the sense coils S_1 through S_9, are used in total. However, the present invention is not limited to that, and the number of sense coils may be set in accordance with the number of variables to be determined. For example, where a total of at least six variables of the location (x, y, z) of the source coil 102a and the direction (Mx, My, Hz) of the magnetic moment are to be determined, at least six sense coils S should be used. By detecting the direction of the magnetic moment of the source coil 102a, the orientation of the end portion 102 can be determined.

Each sense coil S is a magnetic sensor that contains a coil capable of detecting the intensity and direction of the magnetic field in the y-axis direction, for example. However, each sense coil S is not limited to that, and may be formed with the use of a magnetic sensor formed by a magnetoresistive element, a magnetic impedance element (MI element), or the like. Also, each sense coil S can be formed by a three-axis magnetic sensor that includes three coils for detecting the x-axis, the y-axis, and the z-axis, or the like.

The location acquiring unit 220 reads a voltage change caused in each sense coil S as a detection signal, and, based on that, calculates the location of the source coil 102a or the end portion 102. Specifically, the location acquiring unit 220 includes a signal processing unit 221 and a location calculating unit 222. The signal processing unit 221 reads a voltage change caused in each sense coil S as a detection signal, and performs processing such as amplification, filtering, or an A-D conversion on the detection signal. The location calculating unit 222 performs a convergence calculation by an iterative operation using the least-square method, to detect the location and orientation of the source coil 102a or the end portion 102. Specifically, the location calculating unit 222 hypothetically sets a magnetic moment equivalent to the source coil 102a. The location calculating unit 222 then calculates the differences between an ideal detection signal (an ideal voltage) of the location and orientation of the magnetic moment simulated by this hypothesis and the nine detection signals (the voltage data) that are actually input from the signal processing unit 221. The location calculating unit 222 performs the iterative operation to repeatedly calculate the differences while changing the hypothesis, until the differences become equal to or smaller than a predetermined set value. In this manner, the location calculating unit 222 estimates the location of the source coil 102*a*. However, the method of acquiring the location of the end portion 102 is not limited to the above described method, and various other methods may be used.

The information about the location and orientation (hereinafter referred to simply as the location information) acquired by the location calculating unit 222 is input to the control unit 201. The control unit 201 stores the input location information in the storage unit 202. The control unit 201 also reads the stored location information from the storage unit 202, and inputs the location information to the trajectory acquiring unit 230.

The trajectory acquiring unit 230 includes a trajectory generating unit 231, a comparing unit 232, and a scale adjusting unit 233. The location information that is input from the control unit 201 to the trajectory acquiring unit 230 is input to the trajectory generating unit 231. The trajectory generating unit 231 generates the movement trajectory of the end portion 102 by combining the input location information in chronological order, and inputs the information about the movement trajectory to the comparing unit 232.

It should be noted that the generated information about the movement trajectory contains the information about locations in chronological order, which is the information about sequential locations. The information about locations on the movement trajectory may be thinned so that the information is about locations located at predetermined intervals (at 1-cm intervals, for example). This can be done by various kinds of methods, such as a method of thinning the information about locations generated so that the location information becomes information about locations located at the predetermined intervals, or a method of generating the movement trajectory using the location information about locations located at the predetermined intervals. By thinning the information about locations in this manner, the load of the operation using the movement trajectory can be reduced.

Figure 3:
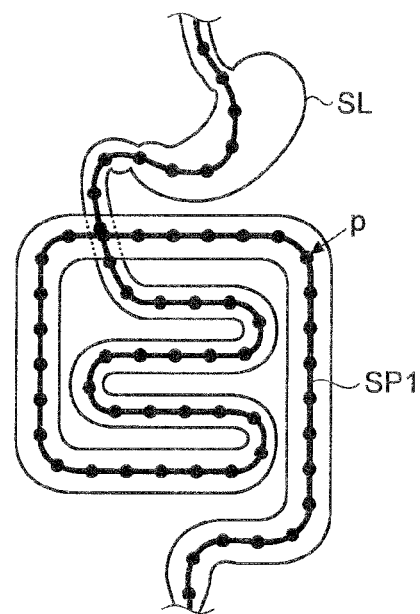
FIG. 3 is a diagram showing a standard trajectory generated from a lumen of a standard subject in the first embodiment.

Also, a movement trajectory as a standard stored beforehand in the storage unit 202 (hereinafter referred to as the standard trajectory SP1) is input to the comparing unit 232 via the control unit 201. This standard trajectory SP1 is not of a specific subject 900, as illustrated in FIG. 3, for example, but is a line formed by copying a lumen SL of a standard subject and connecting center points of the lumen SL. FIG. 3 is a diagram showing the standard trajectory SP1 generated from the lumen SL of a standard subject in the first embodiment. The standard trajectory SP1 contains the information about locations P sequentially located at predetermined intervals (at 1-cm intervals, for example).

The comparing unit 232 determines whether the number of pieces of information about locations included in the movement trajectory that is input from the trajectory generating unit 231 is larger than a threshold value. If the number of pieces of information about the locations included in the movement trajectory is larger than the threshold value, the comparing unit 232 compares the movement trajectory generated so far, that is, the movement path to the current location with the standard trajectory, and inputs the results of the comparison as well as the information about the movement trajectory and the standard trajectory to the scale adjusting unit 233. It should be noted that the threshold value can be such a number of pieces of location information that the movement trajectory generated with the use of the information about the locations up to the current location has such a length as to represent the feature portions of the shape of an organ in the subject 900.

The results of the comparison between the movement trajectory and the standard trajectory can be obtained by extracting the geometrical feature portions from the shape of the lumen of the movement trajectory, and comparing the locations and sizes of the feature portions with the locations and sizes of geometrical feature portions of the standard trajectory. The geometrical feature portions of the standard trajectory may be stored beforehand in the storage unit 202, for example.

The comparison between the movement trajectory and the standard trajectory is not limited to the above described, but may be performed by various other methods, such as a method by which points starting from a reference location in the movement trajectory are respectively connected to points starting from a reference location in the standard trajectory in sequential order, and calculating the distances between those points as the comparison results. It should be noted that the points mentioned here are the points indicated by the information about locations on the respective trajectories.

Figure 4:
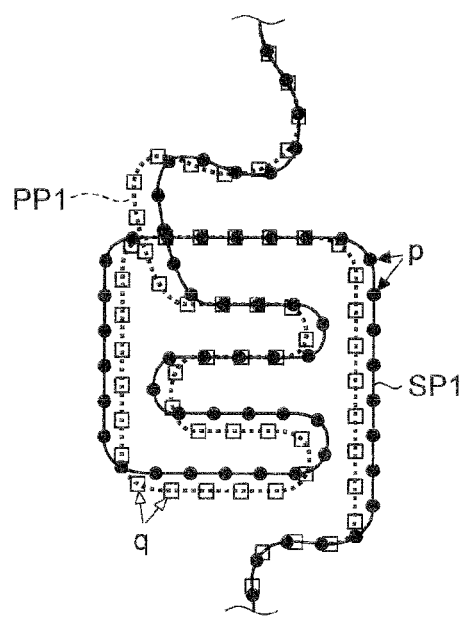
FIG. 4 is a diagram showing an example of a movement trajectory generated by the trajectory generating unit and the standard trajectory held in the storage unit in the first embodiment.
Figure 5:
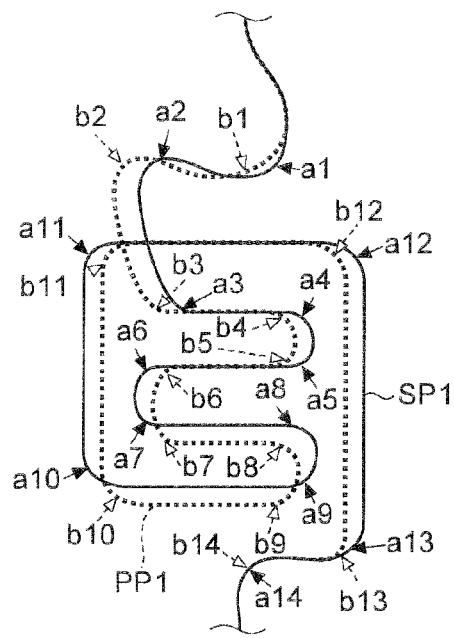
FIG. 5 is a diagram showing the feature portions of a movement trajectory prior to scale adjustment and the standard trajectory according to the first embodiment.
Figure 6:
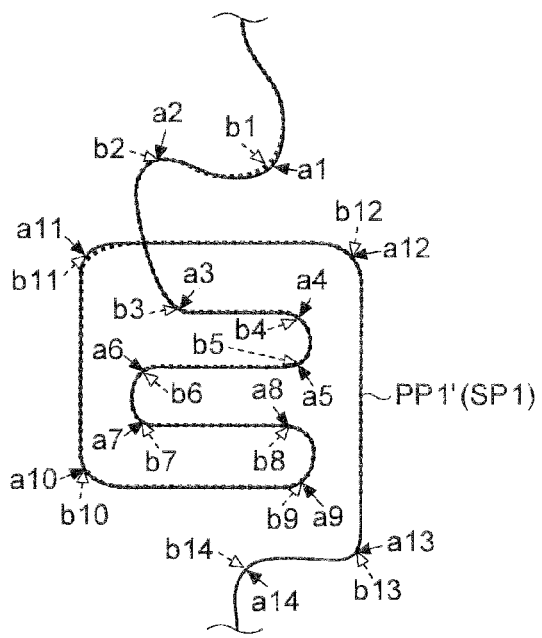
FIG. 6 is a diagram showing the movement trajectory after the scale adjustment and the standard trajectory according to the first embodiment.

Based on the comparison results that are input from the comparing unit 232, the scale adjusting unit 233 entirely and/or partially adjusts the scale of the movement trajectory so that the movement trajectory matches the standard trajectory. Referring now to FIGS. 4 through 6, this process is described in detail. In FIGS. 4 through 6, an example case where an entire movement trajectory PP1 is generated is illustrated, for ease of explanation. FIG. 4 shows examples of the movement trajectory PP1 generated by the trajectory generating unit 231 and the standard trajectory SP1 held in the storage unit 202. FIG. 5 is a diagram showing the feature portions of the movement trajectory PP1 prior to scale adjustment and the standard trajectory SP1. FIG. 6 is a diagram showing the scale-adjusted movement trajectory PP1' and the standard trajectory SP1.

As shown in FIG. 4, the standard trajectory SP1 is formed by connecting a plurality of sequential points p. Meanwhile, the movement trajectory PP1 is formed by connecting a plurality of sequential points q. As is apparent from FIG. 4 showing the standard trajectory SP1 and the movement trajectory PP1 superimposed on each other, the movement trajectory PP1 does not necessarily match the standard trajectory SP1.

Therefore, the comparing unit 232 extracts feature portions (feature portions b1 through b14, for example) of the movement trajectory PP1. The comparing unit 232 then compares the locations and sizes of the feature portions b1 through b14 with the locations and sizes of feature portions (a1 through a14, for example) of the standard trajectory SP1, and also compares the distances between different feature portions of the movement trajectory PP1 and the standard trajectory SP1 respectively, as shown in FIG. 5. The results of the comparisons are input to the scale adjusting unit 233.

Based on the input comparison results, the scale adjusting unit 233 determines the scales of the respective feature portions b1 through b14 and the scales between the respective feature portions b1 through b14. After that, using the determined scales, the scale adjusting unit 233 adjusts the scale of the movement trajectory PP1 at the respective parts. By doing so, the scale adjusting unit 233 adjusts the movement trajectory PP1 to the standard trajectory SP1, as shown in FIG. 6. For example, the scale adjusting unit 233 increases or decreases the scale of the intervals between each two feature portions (b1 through b14) of the movement trajectory PP1 so that the intervals between each two feature portions of the movement trajectory PP1 match the corresponding intervals of the standard trajectory SP1. Also, the scale adjusting unit 233 enlarges or reduces the feature portions b1 through b14 of the movement trajectory PP1 so that the feature portions b1 through b14 of the movement trajectory PP1 match the corresponding feature portions a1 through a14 of the standard trajectory SP1 in size, for example. The information about the scale-adjusted movement trajectory PP1' is input to the control unit 201, and is then transmitted to the display device 280 via the communication interface 205 or is stored into the storage unit 202, for example.

Figure 7:
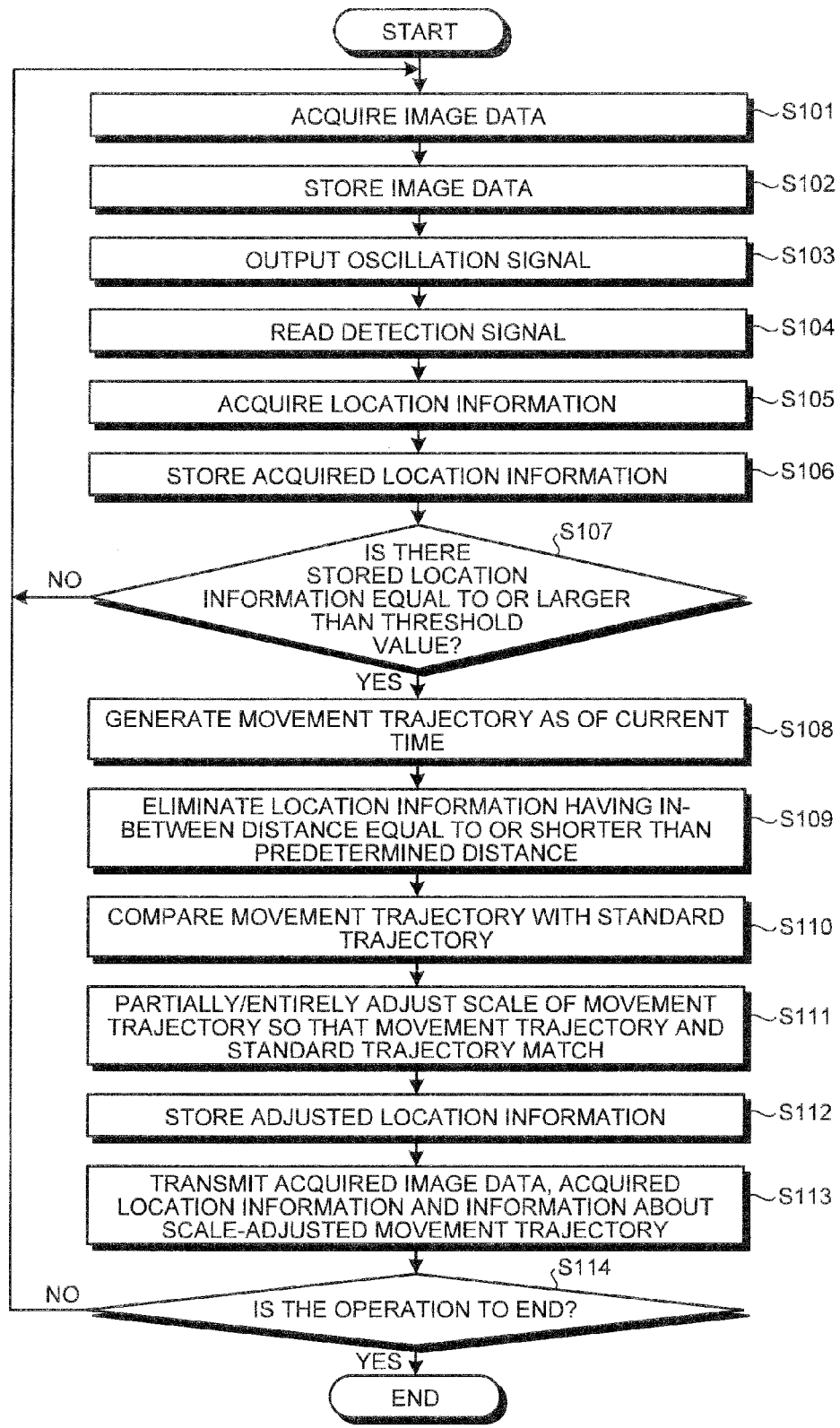
FIG. 7 is a flowchart showing an example of an operation of the receiving device according to the first embodiment.

The operation of the receiving device 200 is now described in detail, with reference to a drawing. FIG. 7 is a flowchart showing an example of the operation of the receiving device 200.

As shown in FIG. 7, the receiving device 200 first activates the image acquiring unit 240 to acquire image data from the operating unit 110 (see FIGS. 1 and 2) of the endoscope 100 (step S101), and stores the acquired image data into the storage unit 202 or the like via the control unit 201 (step S102). It should be noted that a time stamp indicating the imaging time is attached to the image data.

The receiving device 200 then inputs a control signal to the oscillator circuit 210, and causes the oscillator circuit 210 to output a sinusoidal signal at a predetermined frequency (step S103). It should be noted that the sinusoidal signal is input to the cables 1031, and is then input from the cables 1031 to the source coil 102a of the end portion 102 via the operating unit 110 and the signal line 1031a. As a result, the magnetic field FS centering around the source coil 102a (i.e., the end portion 102) is generated.

The receiving device 200 then activates the signal processing unit 221 of the location acquiring unit 220 to read the detection signals from the respective sense coils S (step S104). The receiving device 200 then activates the signal processing unit 221 and the location calculating unit 222 to acquire the location information (the latest location information) about the current location of the source coil 102a (i.e., the end portion 102) from the read detection signals (step S105). The receiving device 200 also stores the acquired location information into the storage unit 202 or the like via the control unit 201 (step S106).

The receiving device 200 then causes the control unit 201 to determine whether the location information stored in the storage unit 202 or the like is equal to or larger than a threshold value that is set in advance (step S107). If the determination result indicates location information equal to or larger than the threshold value is not stored (No in step S107), the receiving device 200 returns to step S101, and again acquires and stores image data and location information.

The result of determination in step S107 indicates that location information equal to or larger than the threshold value is stored (Yes in step S107), on the other hand, the receiving device 200 activates the trajectory generating unit 231 to generate the movement trajectory PP1 up to the present from the location information stored in the storage unit 202 or the like (step S108). The receiving device 200 then causes the trajectory generating unit 231 to perform an operation to subtract such points that each two points q connected to each other in chronological order on the generated movement trajectory PP1 has a distance equal to or shorter than a predetermined distance from each other, from the generated movement trajectory PP1 (step S109). As a result, a movement trajectory PP1 formed by such points that each two points has a distance equal to or longer than the predetermined distance (1 cm, for example) but equal to or shorter than twice the predetermined distance from each other can be generated.

The receiving device 200 then inputs the movement trajectory PP1 obtained in step S109 to the trajectory generating unit 231 and the comparing unit 232, inputs the standard trajectory SP1 stored in the storage unit 202 or the like to the comparing unit 232 via the control unit 201, and causes the comparing unit 232 to compare the movement trajectory PP1 with the standard trajectory SP1 (step S110). It should be noted that the comparison in step S110 can be performed by the method described above with reference to FIGS. 4 through 6.

The receiving device 200 then inputs the results of the comparison between the standard trajectory SP1 and the movement trajectory PP1 and the information about the movement trajectory PP1 from the comparing unit 232 to the scale adjusting unit 233, and causes the scale adjusting unit 233 to perform an operation to partially and/or entirely adjust the scale of the movement trajectory so that the movement trajectory PP1 and the standard trajectory SP1 match (step S111). It should be noted that the scale-adjusted movement trajectory PP1' is stored into the storage unit 202 or the like via the control unit 201, for example (step S112).

The receiving device 200 then transmits the image data acquired in step S101, the location information acquired in step S105, and the information about the scale-adjusted movement trajectory P21', to the display device 280 via, the communication interface 205 (step S113). After that, the receiving device 200 determines whether to continue the operation, or, for example, whether an operation end instruction has been input from the display device 280 via the input unit 203 or the communication interface 205 (step S114). If the operation is to be continued (No in step S114), the receiving device 200 returns to step S101. If the operation is not to be continued (Yes in step S114), the receiving device 200 ends this operation.

Figure 8:
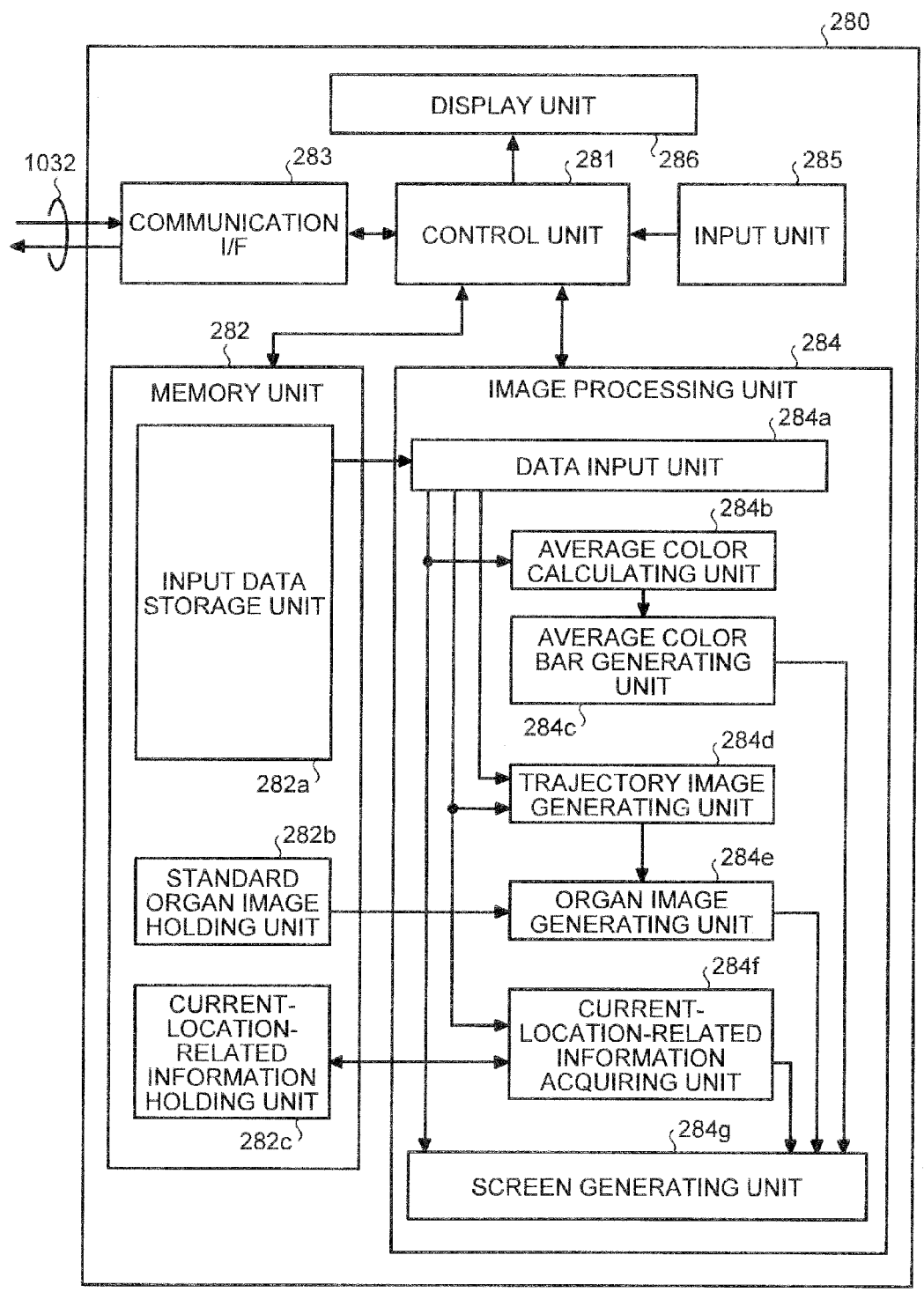
FIG. 8 is a block diagram schematically showing an example structure of the display device according to the first embodiment.
Figure 9:
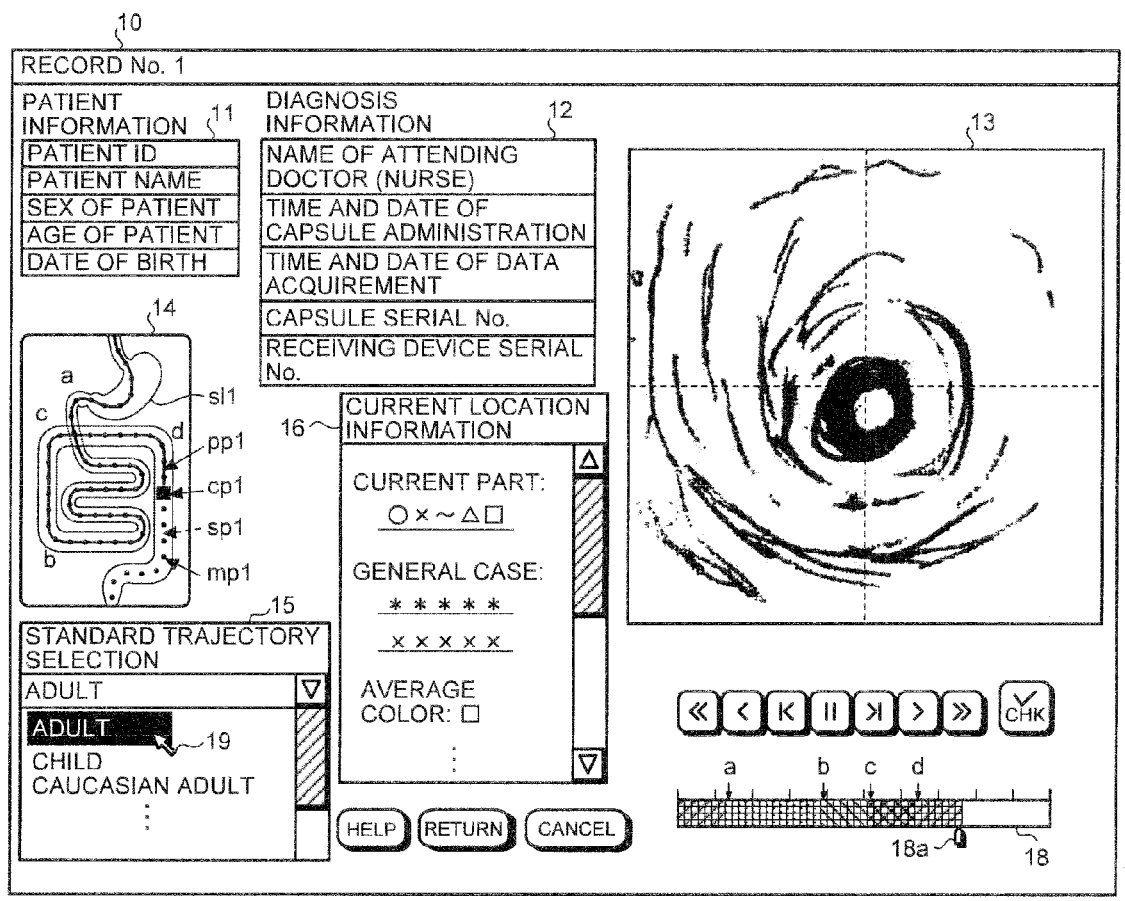
FIG. 9 is a diagram showing an example of a GUI screen generated by the image processing unit in the first embodiment.

The image data, the location information, and the information about the scale-adjusted movement trajectory 221' (these data will be hereinafter referred to as input data) transmitted from the receiving device 200 to the cables 1032 are input to the display device 280 (see FIGS. 1 and 2). An example structure of the display device 280 according to the first embodiment is schematically shown in FIG. 8. FIG. 8 is a block diagram schematically showing the example structure of the display device 280 according to the first embodiment. FIG. 9 is a diagram showing an example of a GUI screen 10 generated by an image processing unit 284 in the first embodiment.

As shown in FIG. 8, the display device includes a control unit 281 that controls the inside of the display device 280, a memory unit 282 that holds various kinds of programs and various kinds of data as needed, a communication interface 283 that exchanges various kinds of data with the receiving device 200 via the cables 1032, an input unit 285 and a display unit 286 that realize a GUI (Graphical User Interface) function for allowing an operator to input various operations and instructions to the display device 280 and the receiving device 200, and the image processing unit 284 that generates the GUI screen 10 (see FIG. 9) that embodies the GUI function to be provided to the operator.

The input data transmitted to the display device 280 via the cables 1032 is input from the communication interface 283 to the control unit 281. The control unit 281 temporarily stores the input data transmitted from the communication interface 283 in a predetermined storage area (an input data storage unit 282a) of the memory unit 282 or the like.

The input data transmitted from the communication interface 283 or the input data stored in the input data storage unit 282a of the memory unit 282 is input to a data input unit 284a of the image processing unit 284 via the control unit 281. In addition to the data input unit 284a, the image processing unit 284 includes an average color calculating unit 284b, an average color bar generating unit 284c, a trajectory image generating unit 284d, an organ image generating unit 284e, a current-location-related information acquiring unit 284f, and a screen generating unit 284g.

The data input unit 284a inputs the image data in the input data to the average color calculating unit 284b and the screen generating unit 284g. The data input unit 284a also inputs the location information in the input data to the trajectory image generating unit 284d and the current-location-related information acquiring unit 284f. The data input unit 284a further inputs the information about the scale-adjusted movement trajectory in the input data to the trajectory image generating unit 284d.

The average color calculating unit 284b calculates the average color of the color components in each set of image data, and inputs the average color to the average color bar generating unit 284c. It should be noted that the average color calculating unit 284b may calculate the average color of the color components of the feature portion in each set of image data. The average color calculating unit 284b may further divide one set (one frame) of image data into several areas (four areas, for example) in the longitudinal direction, for example, and calculate the average color of the color components in each of the divisional areas.

The average color bar generating unit 284c generates an image that visually represents the hues of each set (or each divisional area) of image data in one color, based on the average color of each set (or each divisional area) of image data input from the average color calculating unit 284b, and combines the images in chronological order in accordance with the time stamps attached to the image data. In this manner, the average color bar generating unit 284c generates an average color bar (see an average color bar 18 in FIG. 9) that enables an operator to roughly understand the hues in all the acquired image data at a glance. The generated average color bar 18 is input to the screen generating unit 284g.

Using the information about the scale-adjusted movement trajectory, the trajectory image generating unit 284d generates an image that visualizes the information about the scale-adjusted movement trajectory (see a movement trajectory image pp1 in FIG. 9), and inputs the image to the organ image generating unit 284e. It should be noted that the movement trajectory image pp1 may contain marks mp1 that represent the points left after the thinning. The movement trajectory image pp1 may also contain a mark cp1 that represents the current location of the end portion 102 or the location of the end portion 102 seen when the image data being displayed in a main display area 13 is acquired.

The memory unit 282 also includes a standard organ image holding unit 282b that stores an image of a lumen SL of a standard subject (a standard organ image sl1 in FIG. 9). Using the standard organ image sl1 read from the standard organ image holding unit 282b of the memory unit 282 and the movement trajectory image pp1 input from the trajectory image generating unit 284d, the organ image generating unit 284e generates an organ image display column 14 in the GUI screen 10 shown in FIG. 9, and inputs the organ image display column 14 to the screen generating unit 284g. It should be noted that the standard organ image sl1 may contain a standard trajectory image sp1 that is an image of the standard trajectory SP1.

The memory unit 282 further includes a current-location-related information holding unit 282c that stores information (hereinafter referred to as the current-location-related information) containing the average colors (images), characteristic shapes (images), colors characteristic of residues (images), and colors indicating the characteristics of the blood (images) of the respective feature portions a1 through a14 in an standard lumen, general epidemiological information, and clinical information obtained through the past diagnoses made about the subject 900 to be examined. Based on the current location of the end portion 102 input from the data input unit 284a, the current-location-related information acquiring unit 284f acquires the current-location-related information about a feature portion (one of a1 through a14) in the vicinity of the current location from the current-location-related information holding unit 282c of the memory unit 282, and inputs the current-location-related information to the screen generating unit 284g.

Figure 10:
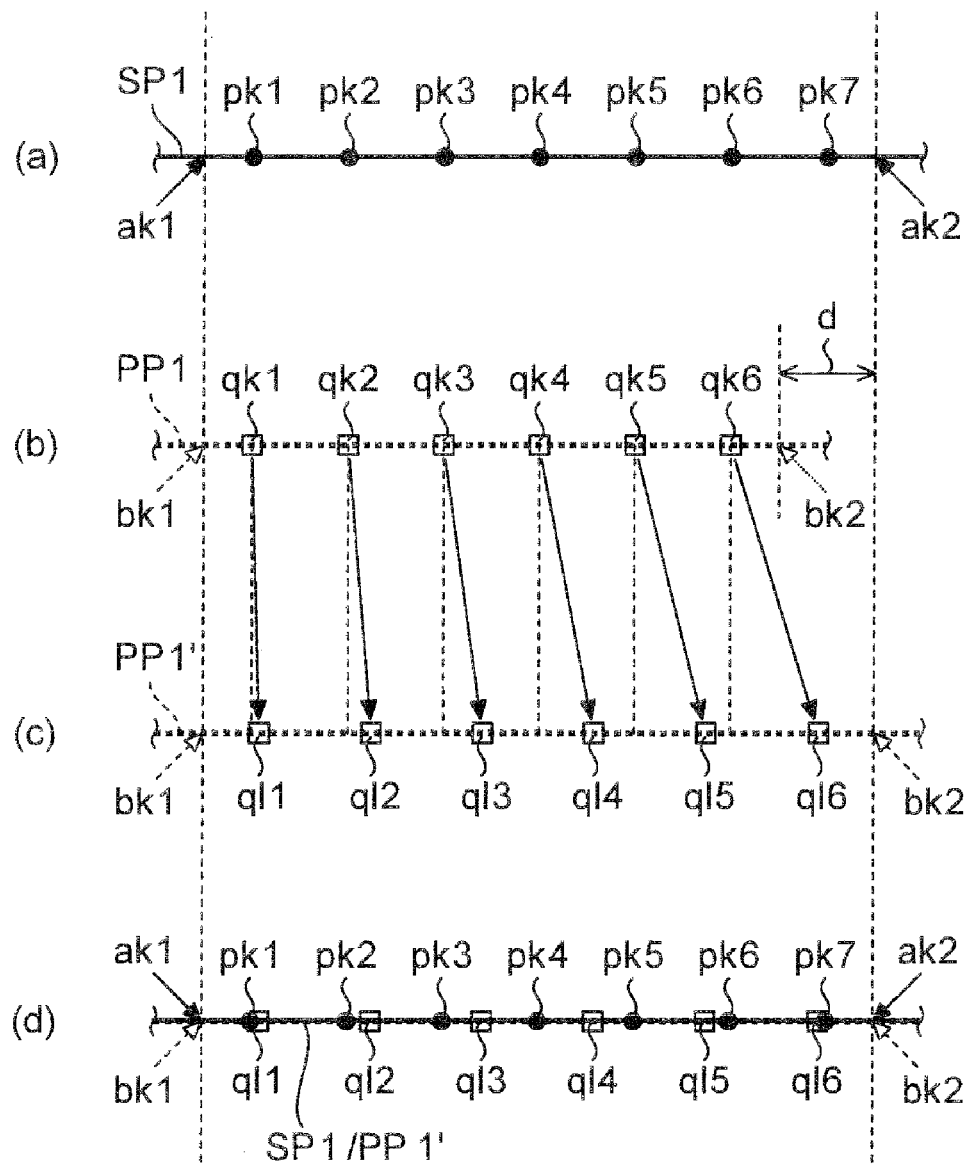
FIG. 10 is a diagram for explaining the relationship between a movement trajectory and the standard trajectory before and after the scale adjustment according to the first embodiment.

In the first embodiment, however, the actually acquired latest location information about the end portion 102 differs from the current location of the end portion 102 on the scale-adjusted movement trajectory PP1'. In a case where feature portions ak1 and ak2 (see FIG. 10(a)) on the standard trajectory SP1 correspond to feature portions bk1 and bk2 (see FIG. 10(b)) on the movement trajectory PP1, respectively, and where the distance between the feature portions bk1 and bk2 is made equal to the distance between the feature portions ak1 and ak2 on the standard trajectory SP1 by adjusting the scale of the movement trajectory PP1, as shown in FIG. 10, the locations of points ql1 through ql6 between the feature portions bk1 and bk2 on the scale-adjusted movement trajectory PP1' differ from the locations of points qk1 through qk6 between the feature portions bk1 and bk2 on the unadjusted movement trajectory PP1, as shown in FIG. 10(c). FIG. 10 is a diagram for explaining the relationship between the standard trajectory and the movement trajectory before and after the scale adjustment according to the first embodiment.

Therefore, in a case where the current-location-related information is acquired based on the unadjusted location information, the current-location-related information acquiring unit 284f cannot always acquire accurate current-location-related information. To counter this problem, the current-location-related information acquiring unit 284f according to the first embodiment identifies the point on the standard trajectory closest to the point indicating the latest location of the end portion 102 on the scale-adjusted movement trajectory PP1', and identifies the current-location-related information associated with the identified current location in the current-location-related information holding unit 282c of the memory unit 282, as shown in FIG. 10(d). In this manner, even where the scale of the movement trajectory PP1 is changed, accurate current-location-related information can be acquired.

Using the image data, the average color bar 18, the standard organ image sl1 (including the movement trajectory image pp1 and the like), and the current-location-related information that have been input, the screen generating unit 284g generates the GUI screen 10 shown in FIG. 9, and displays the GUI screen on the display unit 286 via the control unit 281. In this manner, the GUI function using the GUI screen 10 and the input unit 285 can be provided to the operator. It should be noted that the GUI screen 10 shown in FIG. 9 displays the information about the patient (patient information 11), examination information 12 indicating the results of examinations conducted on the patient, the main display area 13 displaying the latest image data input from the receiving device 200 or image data designated by the operator, the organ image display column 14 displaying the standard organ image sl1 (including the movement trajectory image pp1, including the marks mp1 and cp1, and the standard trajectory image sp1) generated by the organ image generating unit 284e, a current-location-related information display column 16 displaying the current-location-related information corresponding to the current location of the end portion 102 on the standard trajectory SP1, and the average color bar 18. The average color bar 18 has a movable slider 18a that indicates to which point in the average color bar 18 the image data being displayed in the main display area 13 corresponds.

A standard trajectory selection column 15 for providing a GUI function described above that switches standard trajectories SP1 is also incorporated into the GUI screen 10. The standard trajectory selection column 15 displays a pull-down selection menu, for example. The operator handles a pointer 19, using a mouse of the input unit 285 or the like, and selects the standard trajectory applicable to the patient. The standard trajectories to be selected can be created based on the lengths, sizes, shapes, and the like of respective organs that depend on whether the subject is an adult or a child, whether the subject is a man or a woman, or to which racial group the subject belongs, for example.

Figure 11:
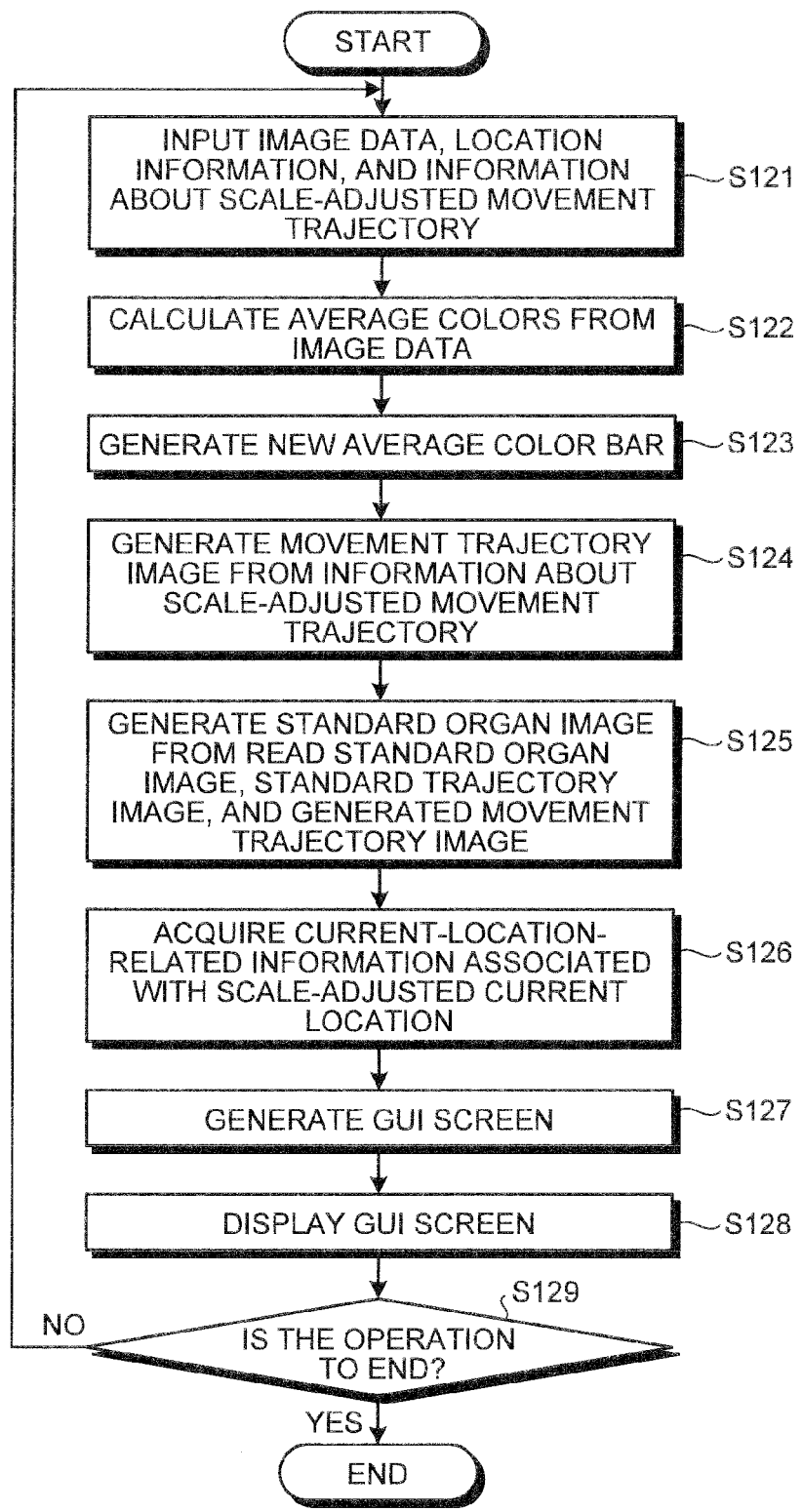
FIG. 11 is a flowchart showing an example of an operation of the display device according to the first embodiment.

Next, the operation of the display device 280 is described in detail, with reference to a drawing. FIG. 11 is a flowchart showing an example of the operation of the display device 280.

As shown in FIG. 11, the display device 280 first receives the image data, the location data, and the information about the scale-adjusted movement trajectory from the receiving device 200 via the cables 1032 (step S121). The display device 280 then inputs the image data from the data input unit 284a of the image processing unit 284 to the average color calculating unit 284b, and causes the average color calculating unit 284b to calculate the average colors of the respective sets of image data (step S122). The display device 280 then inputs the generated average colors to the average color bar generating unit 284c, and causes the average color bar generating unit 284c to generate the average color bar 18 (step S123).

The display device 280 then inputs the information about the scale-adjusted movement trajectory from the data input unit 284a of the image processing unit 284 to the trajectory image generating unit 284d, and causes the trajectory image generating unit 284d to generate the scale-adjusted movement trajectory image pp1 (step S124). The display device 280 then inputs the generated movement trajectory image pp1 to the organ image generating unit 284e, inputs the standard organ image and the standard trajectory image from the standard organ image holding unit 282b of the memory unit 282 to the organ image generating unit 284e, and causes the organ image generating unit 284e to generate the standard organ image sl1 by using the standard organ image and the standard trajectory image (step S125).

The display device 280 then inputs the location information from the data input unit 284a of the image processing unit 284 to the current-location-related information acquiring unit 284f, and causes the current-location-related information acquiring unit 284f to acquire the current-location-related information associated with the scale-adjusted current location of the end portion 102 (step S126).

The display device 280 then inputs the image data from the data input unit 284a of the image processing unit 284 to the screen generating unit 284g, and generates the GUI screen 10 shown in FIG. 9 from the average color bar 18 generated in step S123, the standard organ image sl1 generated in step S125, and the current-location-related information acquired in step S126 (step S127). The display device 280 then inputs the GUI screen 10 to the display unit 286, and displays the GUI screen 10 (step S128). In this manner, the GUI function using the GUI screen 10 and the input unit 285 is provided to the operator.

After that, the display device 280 determines whether to continue the operation, or whether an operation end instruction has been input from the input unit 285, for example (step S129). If the operation is to be continued (No in step S129), the display device 280 returns to step S121. If the operation is not to be continued (Yes in step S129), the display device 280 ends the operation.

With the above described structure and operations, a movement trajectory currently acquired (the first movement trajectory) can be adjusted to an existing standard trajectory (the second movement trajectory) in the first embodiment. Accordingly, the first embodiment can realize the endoscope system 1 that enables an observer to accurately identify observed regions, regardless of the knowledge, experience, and expertise of the observer, by linking predetermined parts (the points p) on the existing standard trajectory (the second movement trajectory) with relevant information (the current-location-related information) about the observed regions.

Second Embodiment

Next, the structure and operations of a second embodiment of the present invention are described in detail, with reference to the accompanying drawings. In the second embodiment, an example case where a capsule endoscope 20 is used as a body-insertable apparatus is described. The capsule endoscope 20 is inserted orally into the subject 900, and performs an imaging operation while moving in a lumen 902 (see FIG. 12) from an esophagus to an anus of the subject 900. In this manner, the capsule endoscope 20 acquires images of the inside of the subject 900. However, the present invention is not limited to that, and it is possible to make various modifications, such as a case where a capsule endoscope that floats on a liquid stored in the stomach, small intestine, or large intestine of the subject 900 is used. In the following description, the same components as those of the first embodiment and its modifications are denoted by the same reference numerals as those used in the first embodiment and its modifications, and, for simplification of explanation, detailed explanation of them is not provided herein.

FIG. 12 is a schematic view showing an example structure of an endoscope system 2 according to the second embodiment. As shown in FIG. 12, the endoscope system 2 includes: the capsule endoscope 20 to be inserted orally into the subject 900; a receiving device 400 that exchanges image data, control commands, and the like with the capsule endoscope 20 by performing wireless communications with the capsule endoscope 20; and a display device 280 that performs predetermined processing on image data received from the capsule endoscope 20 by the receiving device 400, and displays the image data to an operator. It should be noted the receiving device 400 and the display device 280 are external devices placed outside the subject 900. The display device 280 may be the same as that of the first embodiment.

A portable recording medium 290 such as a flash memory or a smart card (a registered trade name) can be attached to and detached from the receiving device 400. Image data and the like received from the capsule endoscope 20 is stored in the portable recording medium 290. The operator detaches the portable recording medium 290 from the receiving device 400, and inserts the portable recording medium 290 into the display device 280. The operator then performs predetermined operations such as operations to reproduce and convert the image data stored in the portable recording medium 290, using the display device 280

Figure 13A:
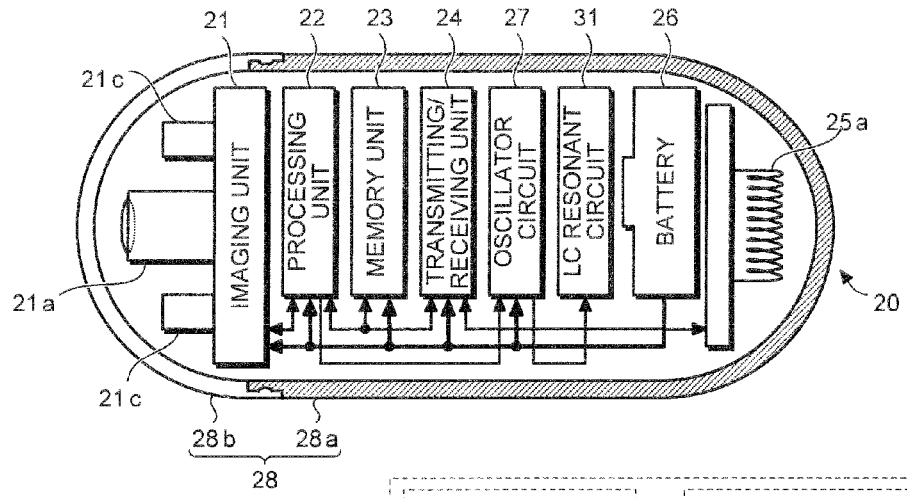
FIG. 13A is a block diagram schematically showing the internal structure of a capsule endoscope according to the second embodiment.
Figure 14:
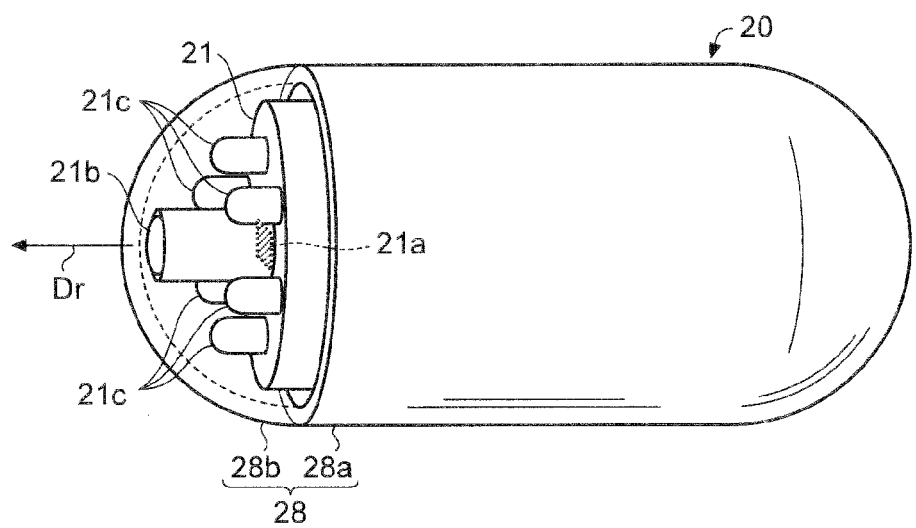
FIG. 14 is a perspective view schematically showing the exterior of the capsule endoscope according to the second embodiment.

Referring now to FIG. 13A and FIG. 14, a schematic example structure of the capsule endoscope 20 is described. FIG. 13A is a block diagram schematically showing the internal structure of the capsule endoscope 20. FIG. 14 is a perspective view schematically showing the exterior of the capsule endoscope 20.

As shown in FIG. 13A, the capsule endoscope 20 includes: an imaging unit 21 that illuminates the inside of the subject 900, and captures images of the inside of the subject 900; a processing unit 22 that performs operations on images generated from the imaging unit 21 and various other operations; a memory unit 23 that stores the image data and the like processed by the processing unit 22; a transmitting/receiving unit 24 and an antenna 25a that exchange signals with the receiving device 400; one or more batteries 26 that supply power to the inside of the capsule endoscope 20; and an oscillator circuit 27 and an LC resonant circuit 31 that generate magnetic fields for location detection. It should be noted that the LC resonant circuit 31 may be replaced with an L (inductor).

The imaging unit 21, the processing unit 22, the memory unit 23, the transmitting/receiving unit 24, the battery 26, the oscillator circuit 27, and the LC resonant circuit 31 are housed in a water-tight casing 28 formed by a container 28a and a cap 28b. As shown in FIG. 14, one end of the container 28a has a hemispherical dome shape, and the other end of the container 28a is open and has a substantially cylindrical shape or a semielliptical shape. On the other hand, the cap 28b has a hemispherical shape, and seals the inside of the casing 28 in a water-tight manner, being fitted into the opening of the container 28a. Also, at least the cap 28b is made of a transparent resin material or the like.

The imaging unit 21 is an imaging means to capture images of the inside of the subject 900. The imaging unit 21 includes: LEDs 21c that illuminate the inside of the subject 900; a CCD array 21a in which CCDs (Charge Coupled Devices) as light receiving elements are arranged in a matrix fashion; a driver circuit (not shown) that drives the LEDs 21c; and a driver circuit (not shown) that drives the CCD array 21a. The imaging unit 21 operates on a regular basis (twice in one second, for example), so as to capture images of the inside of the subject 900 and generate image data. The generated image data is read out by a driver circuit, and is input to the processing unit 22 in substantially real time.

The processing unit 22 performs predetermined signal processing on the input image data, and inputs the processed image data to the transmitting/receiving unit 24. The transmitting/receiving unit 24 functions mainly as an output means to output image data captured by the imaging unit 21 to the external receiving device 400. Therefore, the image data subjected to the predetermined signal processing by the processing unit 22 is wirelessly transmitted in substantially real time from the transmitting/receiving unit 24 to the receiving device 400 via the antenna 25a. However, the present invention is not limited to that, and the image data subjected to the predetermined image signal processing may be stored in the memory unit 23, and may be taken out from the memory unit 23 after the capsule endoscope 20 is pulled out from the subject 900. It should be noted that a time stamp is preferably attached to the transmitted/stored image data by the processing unit 22 or the like, so that the imaging time can be recognized.

As shown in FIGS. 12 through 14, the LEDs 21c and the COD array 21a are placed inside the casing 28 so that the illuminating/imaging direction Dr is directed to the outside of the casing 28 via the transparent cap 28b. The CCD array 21a is placed substantially at the center of a section perpendicular to the longitudinal direction of the casing 28. On the other hand, the plurality of LEDs 21c are arranged to surround the CCD array 21a in the section above.

The antenna 25a of the capsule endoscope 20 is an antenna having directionality, for example. In the second embodiment, a loop antenna is used as the antenna 25a. This antenna 25a having directionality is fixed inside the casing 28.

Figure 13B:
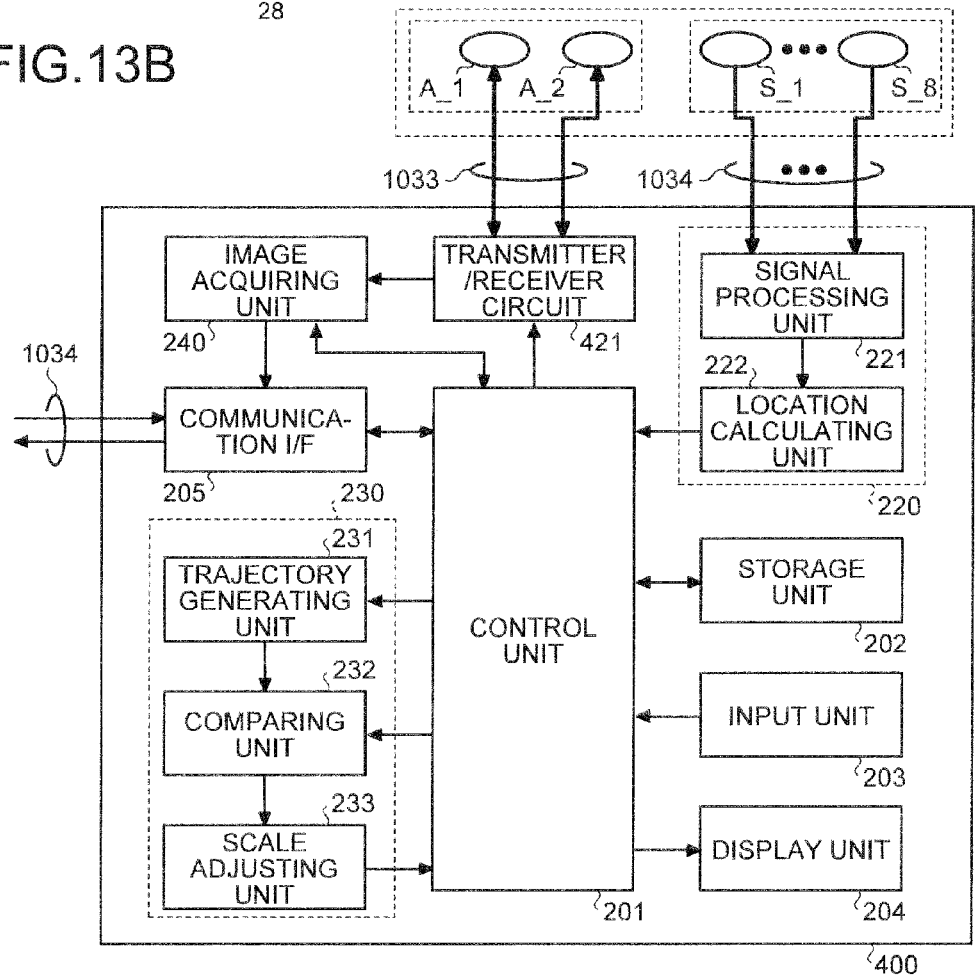
FIG. 13B is a block diagram schematically showing the internal structure of a receiving device according to the second embodiment.

Referring now to FIG. 13B, a schematic example structure of the receiving device 400 according to the second embodiment is described in detail. As is apparent from a comparison between FIG. 13B and FIG. 2, the receiving device 400 has the same structure as the receiving device 200 of the first embodiment, except that the oscillator circuit 210 is replaced with a transmitter/receiver circuit 421.

As shown in FIG. 12 and FIG. 13B, image data that is wirelessly transmitted from the capsule endoscope 20 is received by antennas A_1 and A_2 (hereinafter, arbitrary antennas will be denoted by A) arranged on the body surface of the subject 900, and is input to the receiving device 400 placed outside the subject 900 via cables 1033. The plurality of antennas A are formed by dipole antennas or loop antennas, for example, and are fixed onto the subject 900. However, the number and arrangement pattern of the antennas A, and the sites to which the antennas A are fixed can be changed in various manners.

The image data input from the capsule endoscope 20 via the antennas A is input to the transmitter/receiver circuit 421. After subjected to predetermined signal processing, the image data thereof is input to the control unit 201. The capsule endoscope 20 also includes the oscillator circuit 27 that oscillates to input a sinusoidal signal at a predetermined frequency to the LC resonant circuit 31, and the LC resonant circuit 31 that generates a magnetic field at a predetermined frequency around the oscillator circuit 27 in accordance with the sinusoidal signal at the predetermined frequency (the magnetic field is equivalent to the magnetic field FS of the first embodiment, and will be hereinafter referred to as the resonant magnetic field). The resonant magnetic field generated by the LC resonant circuit 31 is detected by sense coils S_1 through S_9 (hereinafter arbitrary sense coils will be denoted by S) that are fixed onto the subject 900 or are fixed outside the subject 900. After that, as in the above described first embodiment, the resonant magnetic field is used to acquire the location and orientation of the capsule endoscope 20 by the location acquiring unit 220. It should be noted that the method of acquiring a location from a magnetic field that the subject of the location detection has spontaneously generated as above is called an active method.

As described above, in the second embodiment, image data acquired from the capsule endoscope 20, and the location information about the capsule endoscope 20 acquired by the location acquiring unit 220 are input to the control unit 201 of the receiving device 400. The control unit 201 performs the same operation as the operation described in the above first embodiment, so as to cause the trajectory generating unit 231 to generate a movement trajectory of the capsule endoscope 20. The control unit 201 also compares the movement trajectory generated from the trajectory generating unit 231 with the standard trajectory stored beforehand in the storage unit 202 or the like. Based on the results of the comparison, the control unit 201 partially or entirely adjusts the scale of the movement trajectory, so that the movement trajectory can be adjusted to the standard trajectory. After that, the control unit 201 inputs the image data, the location information, and the information about the scale-adjusted movement trajectory from the communication interface 205 to the display device 280 via cables 1034 or the portable recording medium 290.

Meanwhile, the display device 280 performs the same operation as the operation described in the first embodiment, so as to generate the GUI screen shown in FIG. 9. The display device 280 then displays the GUI screen on the display unit 286, and realizes the GUI function to be provided to the operator.

With the above described structure and operations, movement trajectory currently acquired (the first movement trajectory) can be adjusted to an existing standard trajectory (the second movement trajectory), as in the first embodiment. Accordingly, the second embodiment can realize the endoscope system 2 that enables an observer to accurately identify observed regions, regardless of the knowledge, experience, and expertise of the observer, by linking predetermined parts (the points p) on the existing standard trajectory (the second movement trajectory) with relevant information (the current-location-related information) about the observed regions and the like.

Third Embodiment

Next, the structure and operations of a third embodiment of the present invention are described in detail, with reference to the accompanying drawings. In the third embodiment, an example case where a capsule endoscope 30 is used as a body-insertable apparatus is described. The capsule endoscope 30 is inserted orally into the subject 900, and performs an imaging operation while moving in the lumen 902 from the esophagus to the anus of the subject 900. In this manner, the capsule endoscope 30 acquires images of the inside of the subject 900, as in the second embodiment. In the third embodiment, however, an example case where location detection is performed according to a so-called passive method is described. According to the passive method, an LC resonant circuit is provided in the capsule endoscope 30, for example, and an external magnetic field at a predetermined frequency (hereinafter referred to as the driving magnetic field) is supplied to the LC resonant circuit to generate a resonant magnetic field. The resonant magnetic field is detected, and the location of the LC resonant circuit (or the capsule endoscope 30) is calculated from the detection results (detection signals). In addition to that, an example case where the capsule endoscope 30 is automatically guided along a desired route is described in the third embodiment. However, the present invention is not limited to that, and it is possible to make various modifications, such as a case where a capsule endoscope that floats on a liquid stored in a stomach, small intestine, or large intestine of the subject 900 is used. Also, in the following description, the same components as those of the first and second embodiments are denoted by the same reference numerals as those used in the first and second embodiments, and, for simplification of explanation, detailed explanation of them is not provided herein.

Figure 15:
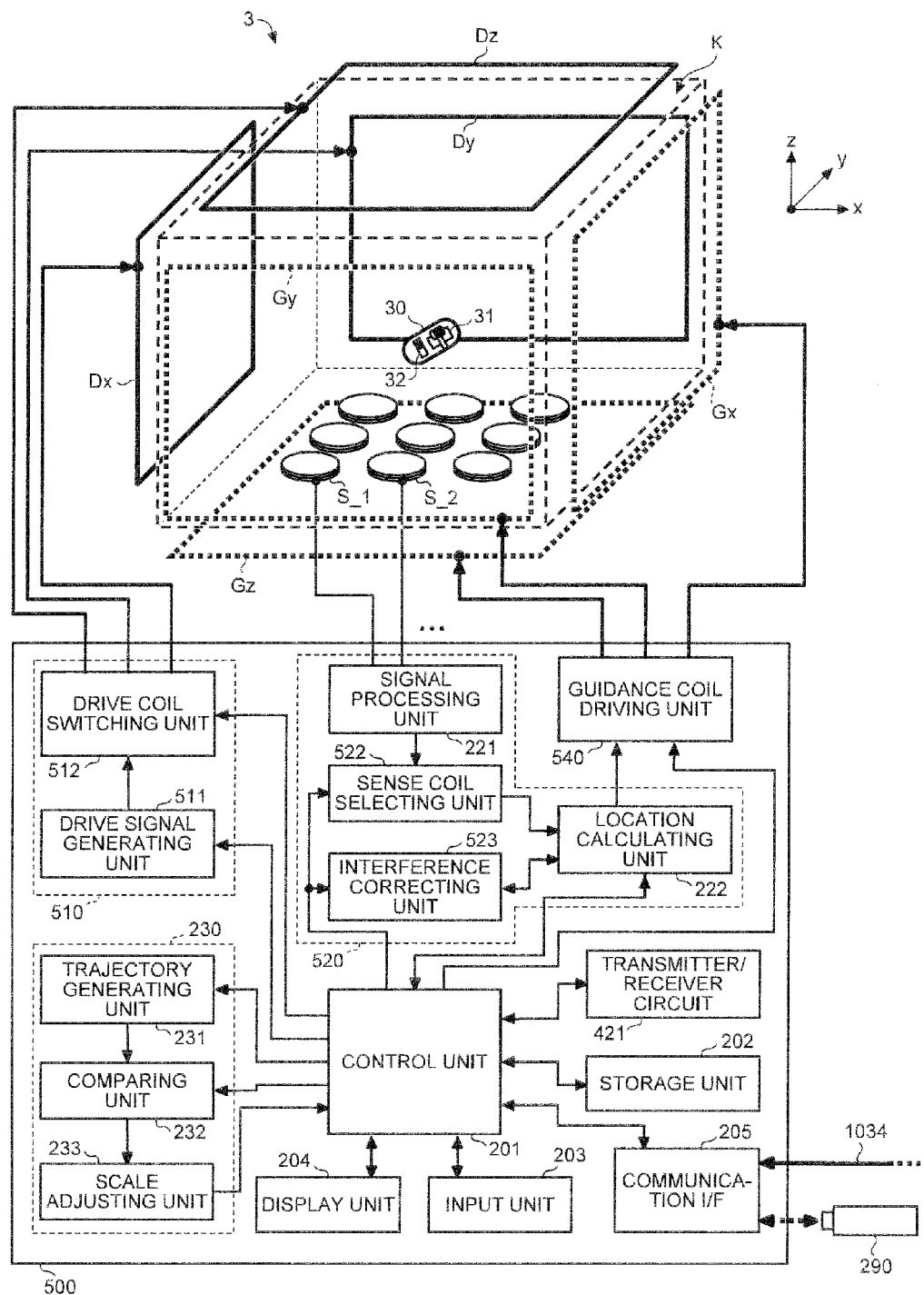
FIG. 15 is a schematic view showing the structure of an endoscope guidance system according to a third embodiment.

FIG. 15 is a schematic view showing the structure of an endoscope guidance system 3 according to the third embodiment. As shown in FIG. 15, the endoscope guidance system 3 includes a detection space K that houses the subject 900 having the capsule endoscope 30 inserted thereinto, and a receiving device 500 that detects the location and orientation (location information) of the capsule endoscope 30 in the detection space K. It should be noted that the endoscope guidance system 3 also includes the display device 280 of the first and second embodiments, but is not shown in FIG. 15, for simplification.

The capsule endoscope 30 has the same structure as that of the second embodiment (see FIG. 13A and FIG. 14), except for an LC resonant circuit 31 and a permanent magnet 32 each fixed to the casing 28. The LC resonant circuit 31 is excited by an external magnetic field (hereinafter referred to as the driving magnetic field) generated at a substantially resonant frequency in the detection space K, and generates a resonant magnetic field for location detection. The permanent magnet 32 acts with external magnetic fields (hereinafter referred to as the guidance magnetic fields) generated in the detection space K, and causes the capsule endoscope 30 to generate a thrust force in the guiding direction.

Also, drive coils Dx, Dy, and Dz (hereinafter, arbitrary drive coils will be denoted by D) that form substantially uniform driving magnetic fields in different directions from one another in the detection space K, and a plurality of sense coils S that detect the resonant magnetic field generated by the LC resonant circuit 31 of the capsule endoscope 30 are provided in the vicinities of the detection space K. Further, guidance coils Gx, Gy, and Gz (hereinafter, arbitrary guidance coils will be denoted by G) that form guidance magnetic fields in different directions from one another in the detection space K are provided in the vicinities of the detection space K. In FIG. 15, however, for clarification, one of the coils in each pair of drive coils D is not shown. Also, the sense coils S provided on the ceiling side of the detection space K are not shown in FIG. 15.

Each drive coil D forms a pair with each corresponding drive coil (not shown) located on the opposite side of the detection space K, and each pair generates a substantially uniform driving magnetic field formed by magnetic field lines extending in the x-, y-, and z-axis directions in the detection space K, for example. Accordingly, by switching the pairs of drive coils D to be driven, that is, switching the directions of driving magnetic fields in accordance with the location and orientation of the capsule endoscope 30, the LC resonant circuit 31 can be caused to generate a resonant magnetic field with stable intensity, regardless of the direction in which the LC resonant circuit 31 (particularly the inductor (L)) of the capsule endoscope 30 lies in the detection space K. As a result, the accuracy of location detection of the capsule endoscope 30 can be improved.

Each guidance coil G forms a pair with each corresponding guidance coil (not shown) located on the opposite side of the detection space K, and each pair forms a guidance magnetic field for guiding the capsule endoscope 30 toward a desired location or in a desired direction is formed in the detection space K in accordance with the location and orientation of the capsule endoscope 30 (particularly the permanent magnet 32). In the following, for simplification of explanation, the guidance coils G shown in the drawing are described.

The receiving device 500 includes a drive coil input signal adjusting unit 510, a location acquiring unit 520, and a guidance coil driving unit 540, as well as the control unit 201, the storage unit 202, the input unit 203, the display unit 204, the communication interface 205, the location calculating unit 222, the trajectory acquiring unit 230, and the transmitter/receiver circuit 421.

The drive coil input signal adjusting unit 510 includes: a drive signal generating unit 511 that generates a drive signal, based on a signal that is input from the control unit 201; and a drive coil switching unit 512 that switches the drive coils D to which the drive signal is input, under control of the control unit 201, for example.

The location acquiring unit 520 includes the signal processing unit 221, a sense coil selecting unit 522, an interference correcting unit 523, and the location calculating unit 222, for example. The sense coil selecting unit 522, under control of the control unit 201, selects a sense coil S from which the signal processing unit 221 is to read a detection signal, from the plurality of sense coils S, for example.

The signal processing unit 221 regularly or irregularly reads a voltage change caused in each sense coil S as a detection signal, and performs processing such as amplification, filtering, or an A-D conversion on the detection signal, as in the first embodiment. Detection signals subjected to the signal processing are input to the location calculating unit 222 via the sense coil selecting unit 522. From the detection signals input via the sense coil selecting unit 522 and the already calculated location information about the capsule endoscope 30, the location calculating unit 222 and the interference correcting unit 523 calculate more accurate location information about the capsule endoscope 30 through a convergence calculation.

Here, the detection signals read from the sense coils S contain the components of a driving magnetic field substantially equal to the resonant frequency of the LC resonant circuit 31. The resonant magnetic field generated by the LC resonant circuit 31 has a phase difference of 90° with respect to the driving magnetic field. Therefore, to remove the components of the driving magnetic field from the components of magnetic fields contained in interference-corrected detection signals, vector components having phase differences of 90° with respect to the driving magnetic field need to be extracted from the detected magnetic fields.

Therefore, in the third embodiment, before the location detection is actually performed, a driving magnetic field is generated in the detection space K by driving the drive coils D while the LC resonant circuit 31 is not introduced in the detection space K, and the amplitudes and phase components of the driving magnetic fields actually detected by the sense coils S and a magnetic field sensor (not shown) placed in the detection space K are calculated in that situation. After that, the magnetic field components (the vector quantities) already calculated are subtracted, through a vector operation, from the detected magnetic fields obtained by introducing the LC resonant circuit 31 into the detection space K, so as to determine the components of the resonant magnetic field (a calibration process). In this embodiment, based on the resonant magnetic field obtained as above, the location and direction of the LC resonant circuit 31 are determined by a convergence calculation using the least-square method.

However, the detection signals read from the sense coils S contain unnecessary magnetic field components such as those of magnetic fields generated by the drive coils D or the like interfering with the magnetic fields generated in the detection space K. The unnecessary magnetic fields are generated by the interference with coils placed near the detection space K, such as the interference between the LC resonant circuit 31 and the guidance coils G. Therefore, the unnecessary magnetic fields have the substantially same frequency as the resonant magnetic field.

Therefore, in the third embodiment, the interference correcting unit 523 performs an operation (a correcting operation) to eliminate errors due to unnecessary magnetic field components contained in the detection signals from the location information calculated by the location calculating unit 222. The correcting operation may be performed by registering correction amounts corresponding to locations and orientations beforehand in an LUT or the like. However, the present invention is not limited to that, and unnecessary magnetic field components may be calculated in accordance with locations and orientations when necessary.

According to the method by which correction amounts are registered beforehand in an LUT, unnecessary magnetic field components generated by the respective drive coils D are obtained beforehand through a simulation or actual measurement, for example. To perform a simulation, a current detecting unit for detecting a current flowing in each drive coil D may be provided. The simulation may be performed with the use of current values detected by the current detecting unit. The obtained information is associated with locations and orientations, and is managed as the correction amounts in an LUT or the like. The interference correcting unit 523 refers to the LUT, using the already calculated locations and orientations. The interference correcting unit 523 then acquires the correction amounts corresponding to the locations and orientations, and corrects the detection signals with the use of the correction amounts. The interference-corrected detection signals are input to the location calculating unit 222.

The location calculating unit 222 refers to the LUT in a location calculation, and acquires the phase components of the driving magnetic fields to be removed from the magnetic field components contained in the interference-corrected detection signals. Based on the phases, the location calculating unit 222 corrects the detection signals, and extracts the resonant magnetic field (a calibration process). To detect the location of the LC resonant circuit 31 (i.e., the capsule endoscope 30), a convergence calculation using the least-square method can be used, as in the first embodiment.

Figure 16:
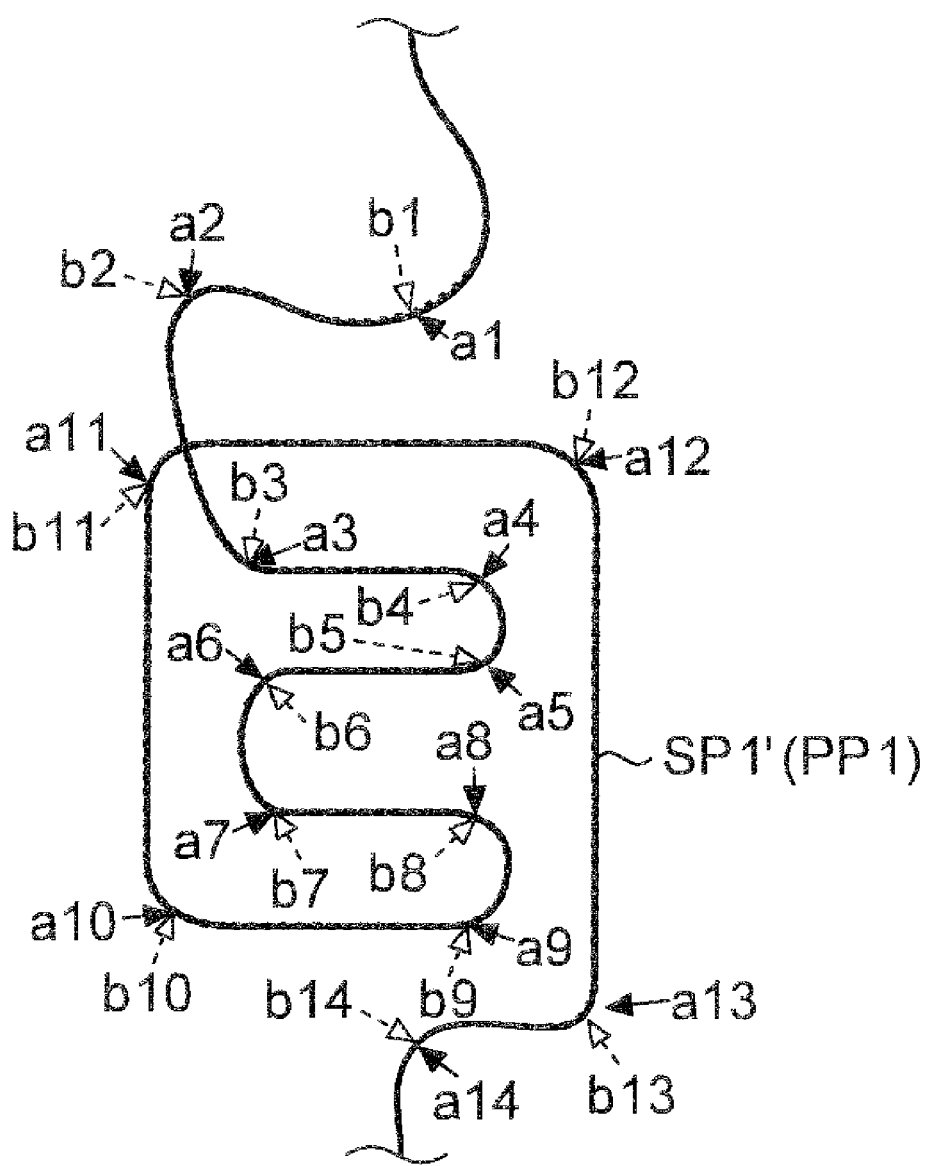
FIG. 16 is a diagram showing a movement trajectory and a standard trajectory after scale adjustment according to the third embodiment.

The guidance coil driving unit 540 and the guidance coils G form an inductance magnetic field to act on the permanent magnet 32 fixed to the capsule endoscope 30 in the detection space K, and guide the capsule endoscope 30. In the third embodiment, the guidance coil driving unit 540 and the guidance coils G guide the capsule endoscope 30 along the standard trajectory. Therefore, in the third embodiment, the trajectory generating unit 231 adjusts the standard trajectory SP1 to the movement trajectory PP1 (the movement trajectory PP1 up to the present only) so that the standard trajectory PP1 and the movement trajectory SP1 substantially match. The information about the generated movement trajectory PP1 and the scale-adjusted standard trajectory SP1' is input to the guidance coil driving unit 540. FIG. 16 is a diagram showing the movement trajectory PP1 and the scale-adjusted standard trajectory SP1' according to the third embodiment.

Based on the latest location information that is input from the location calculating unit 222, and the information about the movement trajectory and the scale-adjusted standard trajectory that is input from the trajectory generating unit 230, the guidance coil driving unit 540 identifies the next point p (see FIG. 3 and FIG. 4) on the scale-adjusted standard trajectory, with respect to the current location of the capsule endoscope 30 on the movement trajectory PP1 (the standard trajectory SP1).

Figure 17:
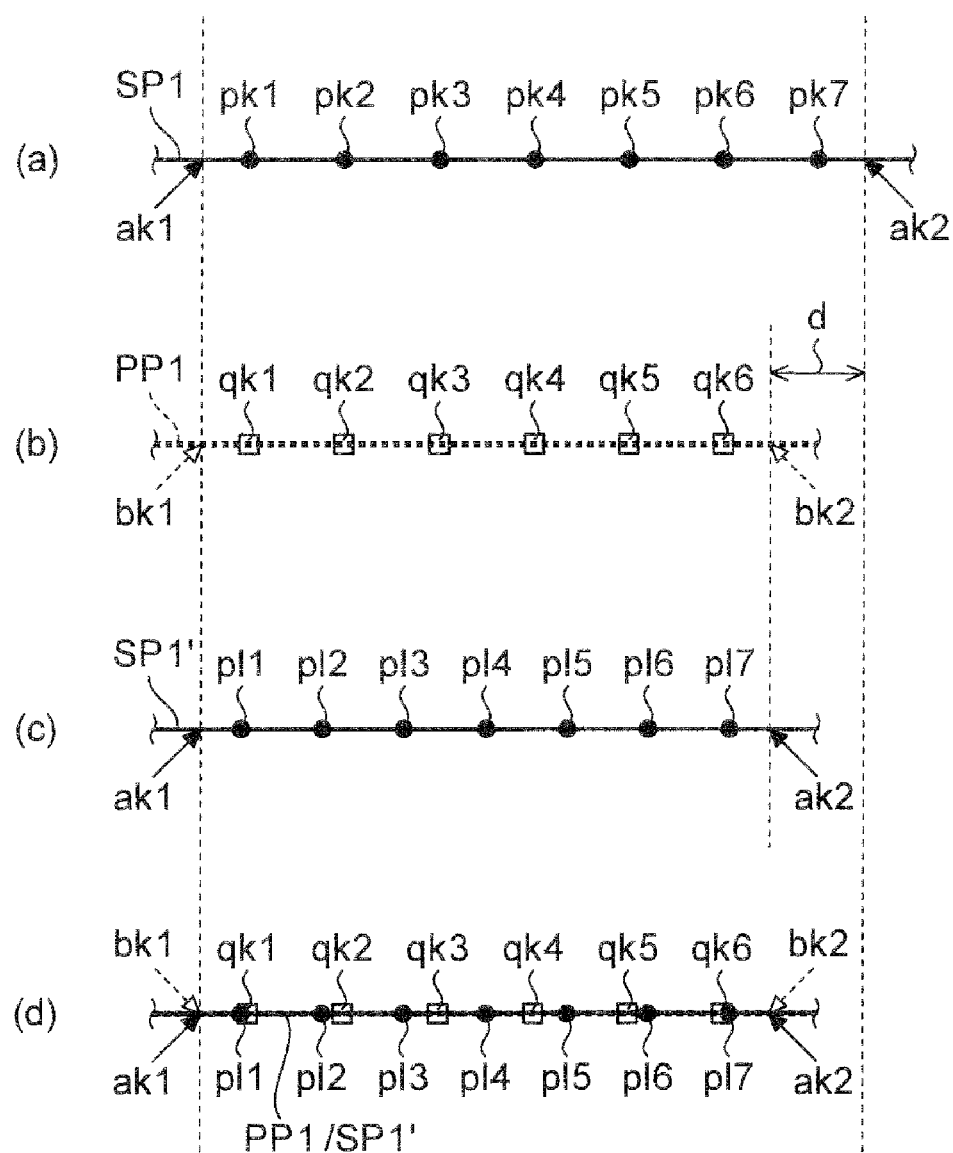
FIG. 17 is a diagram for explaining the relationship between a movement trajectory and the standard trajectory before and after the scale adjustment according to the third embodiment.

For example, as shown in FIG. 17, where feature portions ak1 and ak2 (see FIG. 17(a)) on the standard trajectory SP1 correspond to feature portions bk1 and bk2 (see FIG. 17(b)) on the movement trajectory PP1, respectively, the scale of the standard trajectory SP1 is adjusted and is made shorter by a distance d, so that the distance between the feature portions ak1 and ak2 is made equal to the distance between the feature portions bk1 and bk2 on the movement trajectory PP1, as shown in FIG. 17(c). In that case, the relationship between the movement trajectory PP1 and the scale-adjusted standard trajectory SP1' is as shown in FIG. 17(d). Where the points qk1 through qk6 on the movement trajectory PP1 are the current location (the latest location information) of the capsule endoscope 30 that sequentially changes, the points pl1 through pl7 that come after the respective points qk1 through qk6 can be the movement targets of the capsule endoscope 30. That is, if the current location of the capsule endoscope 30 is the point qk1, for example, the guidance target of the capsule endoscope 30 is set at one of the points p12 through p17. When the current location of the capsule endoscope 30 passes the point p12 on the scale-adjusted standard trajectory SP1' (or has moved to the location of the point qk2, for example), the guidance target of the capsule endoscope 30 is set at one of the points p13 through p17. Thereafter, the guidance target is pushed further as the capsule endoscope 30 moves ahead, and the capsule endoscope 30 is guided accordingly. In this manner, the capsule endoscope 30 can be guided along the scale-adjusted standard trajectory SP1'. It should be noted that a next guidance target is not necessarily the point p that comes immediately after the current point p, but various modifications may be made. For example, a next guidance target may be the point p ten points after the current point p.

The guidance coil driving unit 540 acquires or generates information (guidance information) for guiding the capsule endoscope 30 to the guidance target specified as above. Based on the information, the guidance coil driving unit 540 generates a guidance signal. The guidance coil driving unit 540 also inputs the generated guidance signal to one or more pairs of guidance coils G as needed. In this manner, a guidance magnetic field for guiding the capsule endoscope 30 to the guidance target is generated in the detection space K.

As the guidance information, it is possible to use various kinds of information, such as target locations and orientations, the target velocity and target angular velocity of the capsule endoscope 30, the target acceleration and target angular acceleration of the capsule endoscope 30.

Further, the guidance information may be associated with the input latest (current) location, orientation, and guidance target of the capsule endoscope 30, and may be registered beforehand in a lookup table, for example. However, the present invention is not limited to that and, for example, vectors that represent the required travel distance and the required change in posture of the capsule endoscope 30 that are determined from the input current location, orientation, and target location of the capsule endoscope 30 may be associated with predetermined guidance information, and may be managed in an LUT and the like.

Figure 18:
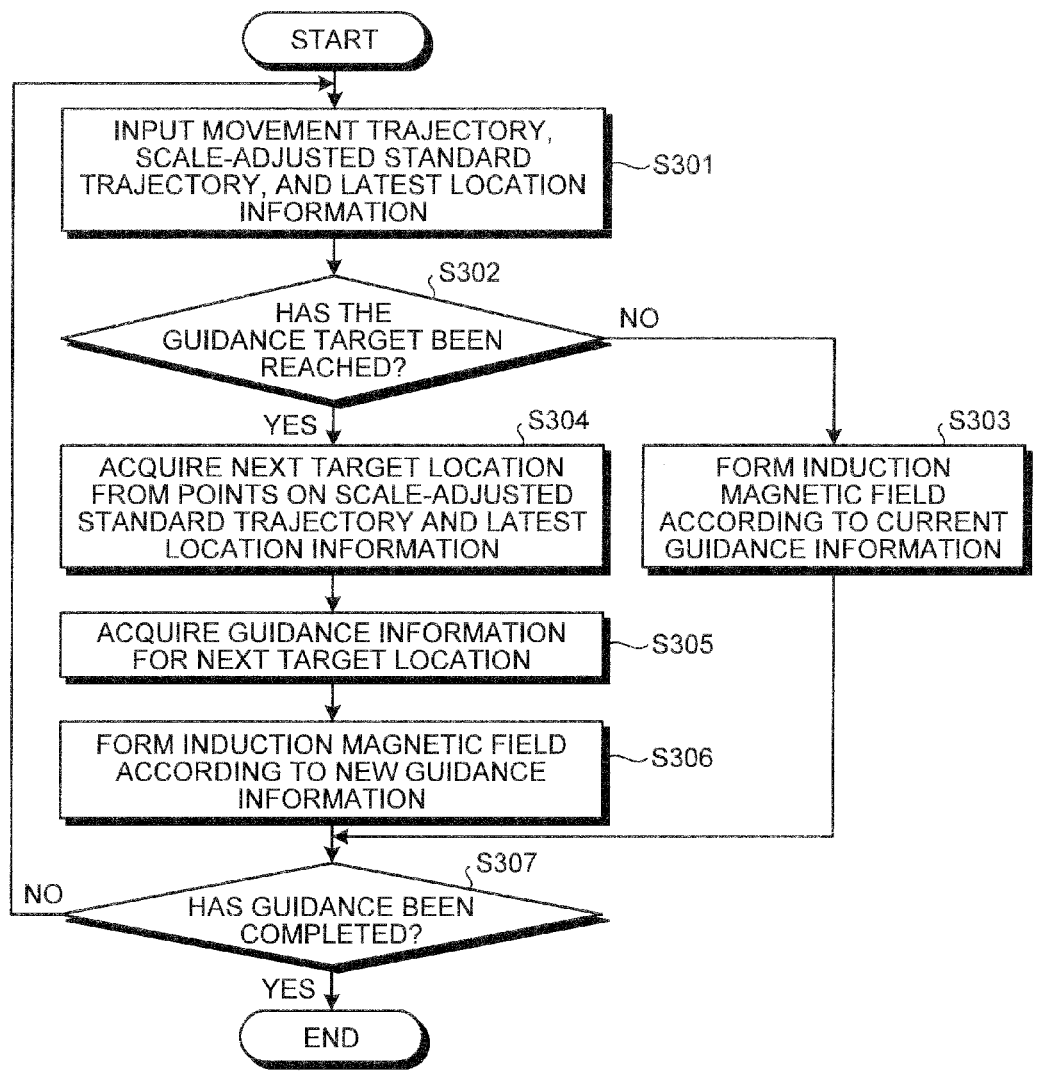
FIG. 18 is a flowchart showing an example of an operation to be performed when the receiving device guides the capsule endoscope according to the third embodiment.

Next, an operation to be performed by the receiving device 500 to guide the capsule endoscope 30 according to the third embodiment is described in detail, with reference to a drawing. FIG. 18 is a flowchart showing an example of the operation to be performed by the receiving device 500 to guide the capsule endoscope 30.

As shown in FIG. 18, the receiving device 500 first inputs the information about the movement trajectory and the scale-adjusted standard trajectory from the trajectory generating unit 230 to the guidance coil driving unit 540, and inputs the latest location information from the location calculating unit 222 to the guidance coil driving unit 540 (step S301). The receiving device 500 then causes the guidance coil driving unit 540 to determine from the latest location information whether the capsule endoscope 30 has reached the point set as the guidance target on the scale-adjusted standard trajectory (step S302). If the capsule endoscope 30 has not reached the point (No in step S302), the receiving device 500 causes the guidance coil driving unit 540 to continue to guide the capsule endoscope 30 to the current guidance target (step S303), and then moves on to step S307.

If the result of the determination in step S302 indicates that the capsule endoscope 30 has reached (or already passed) the guidance target (Yes in step S302), the receiving device 500 causes the guidance coil driving unit 540 to acquire the next guidance target from the points on the scale-adjusted standard trajectory and the latest location information (step S304), and causes the guidance coil driving unit 540 to acquire the guidance information for guiding the capsule endoscope 30 to that point on the scale-adjusted standard trajectory (step S305). The receiving device 500 also causes the guidance coil driving unit 540 to generate a guidance signal for generating a guidance magnetic field in accordance with the acquired guidance information, and input the guidance signal to the guidance coils G to form a guidance magnetic field in the detection space K in accordance with the new guidance information (step S306).

After that, the receiving device 500 determines whether to continue the operation or whether an operation end instruction has been input from the display device 280 via the input unit 203 or the communication interface 205, for example (step S307). If the operation is to be continued (No in step S307), the receiving device 500 returns to step S301. If the operation is not to be continued (Yes in step S307), the receiving device 500 ends this operation.

With the above described structure and operations, the third embodiment can achieve the advantage to automatically guide the capsule endoscope 30 along an existing standard trajectory (the second movement trajectory), as well as the same effects as those of the above described second embodiment.

First Modification

In the above described first and second embodiments, example cases where a movement trajectory is adjusted to the standard trajectory by partially or entirely adjusting the scale of the movement trajectory have been described. However, the present invention is not limited to that, and the standard trajectory may be adjusted to a movement trajectory by partially or entirely adjusting the scale of the standard trajectory, for example. This can be readily done by inverting the positive or negative sign of the amount of adjustment (magnification) of the scale of part of or the entire movement trajectory to be adjusted to the above described standard trajectory. Therefore, detailed explanation is not provided herein.

Second Modification

In the above described first through third embodiments, example cases where a movement trajectory is adjusted to the standard trajectory have been described. However, a current movement trajectory (the first movement trajectory) may be adjusted to a movement trajectory measured in previous detection (the second movement trajectory). In this structure, the storage unit 202 or the like of the receiving device 200/400/500 holds the information about the second movement trajectory that is the previous information, together with the information about the standard trajectory or instead of the information about the standard trajectory. The comparing unit 232 compares the current movement trajectory (the first movement trajectory) with the previous movement trajectory (the second movement trajectory), and inputs the results of the comparison to the scale adjusting unit 233. This can be easily applied to the above described first and second embodiments, and therefore, detailed explanation is not provided herein.

Third Modification

Alternatively, a checkpoint may be set beforehand on the standard trajectory to which a movement trajectory is to be adjusted, and a check can be made to determine whether the end portion 102 of the probe 101 or the capsule endoscope 20/30 has passed the checkpoint. When the end portion 102 or the capsule endoscope 20/30 has passed the checkpoint, the operator can be notified of that. The following is a description of this structure as a third modification of one of the above described first through third embodiments. In the following, however, the third modification is described as a modification of the above described first embodiment.

Figure 19:
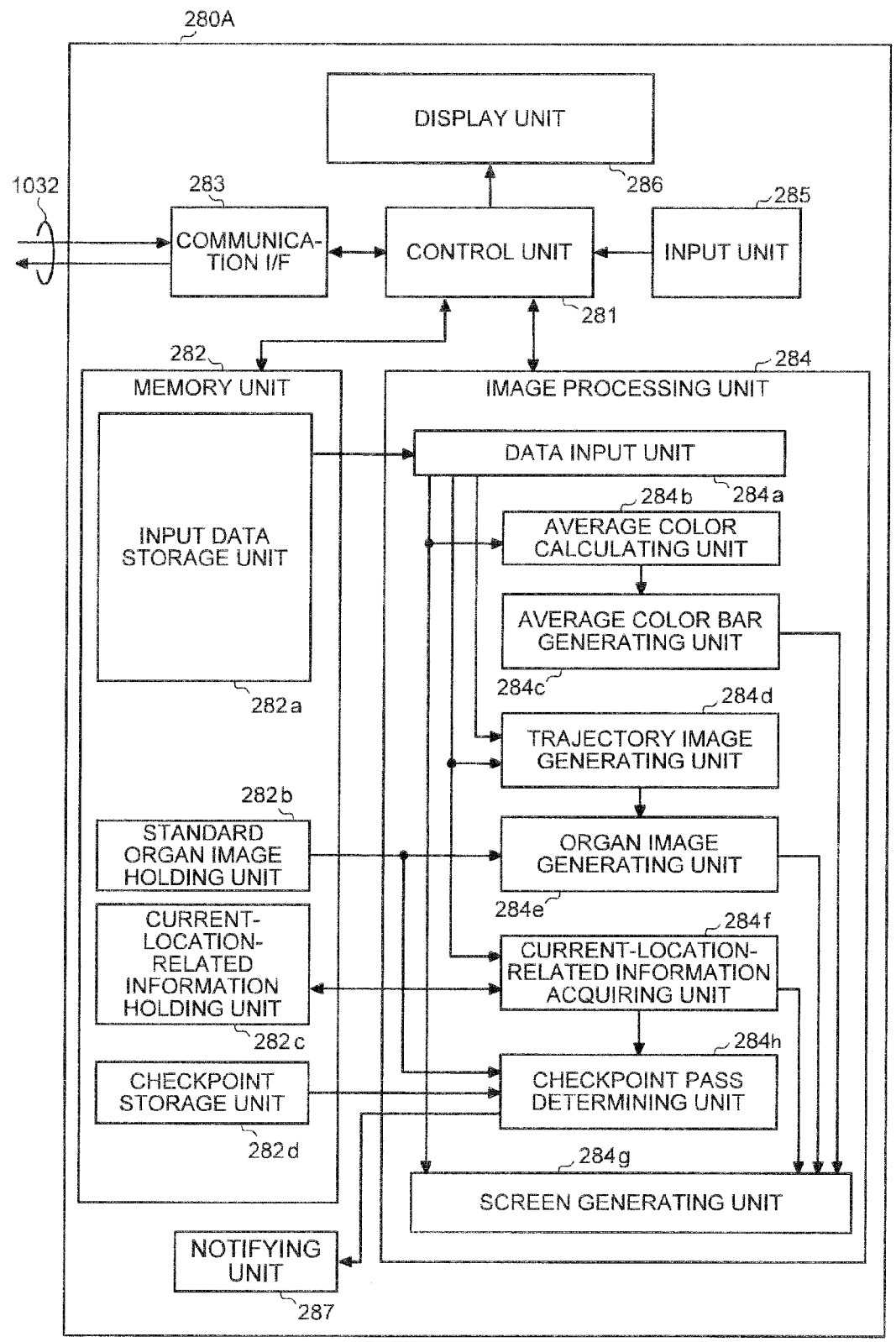
FIG. 19 is a block diagram schematically showing an example structure of a display device according to a third modification of the first embodiment.

FIG. 19 is a block diagram schematically showing an example structure of a display device 280A according to the third modification. As shown in FIG. 19, the display device 280A according to the third modification has the same structure as the display device 280 shown in FIG. 8, except that the memory unit 282 includes a checkpoint storage unit 282d that stores the checkpoint set on the standard trajectory, the image processing unit 284 includes a checkpoint pass determining unit 284h that determines whether the end portion 102 of the probe 101 has passed the checkpoint, and the display device 280A includes a notifying unit 287 that notifies the user that the end portion 102 has passed the checkpoint.

The checkpoint set on the standard trajectory is input from the checkpoint storage unit 282d to the checkpoint pass determining unit 284h, and the information about the current location of the end portion 102 and the information about the standard trajectory are input from the current-location-related information acquiring unit 284f to the checkpoint pass determining unit 284h. From the checkpoint, the current location of the end portion 102, and the standard trajectory, the checkpoint pass determining unit 284h determines whether the end portion 102 has passed a location equivalent to the checkpoint in the subject 900. When determining that the end portion 102 has passed the location, the checkpoint pass determining unit 284h inputs the determination result to the notifying unit 287. Upon receipt of the input about the pass, the notifying unit 287 audibly notifies the operator of the pass, for example.

The checkpoint is input beforehand from the input unit 285 by the operator or the like, and is then stored into the checkpoint storage unit 282d. The notification to the operator may be made with the use of the display unit 286, for example.

With this structure, the operator can be prevented from ending the examination on the subject 900, though the examination has not been completed yet. It should be noted that the checkpoint pass determining unit 284h and the notifying unit 287 may not be provided in the display device 280A, and may be provided in the receiving device 200/400/500, for example.

Fourth Modification

In any one of the above described first through third embodiments, when the values of the average colors stored as the current-location-related information markedly differ from the values of the average colors calculated by the average color calculating unit 284b, the operator can be notified of the differences. This structure can be realized by providing a comparing unit in the control unit 281 or the image processing unit 284, for example. The comparing unit compares the average colors calculated by the average color calculating unit 284b with the average colors contained in the current-location-related information acquired by the current-location-related information acquiring unit 284f. If the values of the average colors calculated by the average color calculating unit 284b markedly differ from the values of the average colors contained in the current-location-related information according to the comparing unit, the operator is notified of the differences through the display unit 286 or a speaker (not shown) or the like.

Fifth Modification

In the above described first through third embodiments, the endoscope 100 or the capsule endoscope 20/30 has been described as an example of a medical device. However, the present invention is not limited to that, and may be applied to various other medical devices, such as tube-type or capsule-type medical devices that perform predetermined treatment on an affected part in the subject 900.

Further, in the above described first embodiment, the location of the end portion 102 of the probe 101 is acquired, and the movement trajectory of the location of the end portion 102 is generated. However, the present invention is not limited to that, and the above described first embodiment can be applied to a medical device that has a plurality of source coils on a middle portion of the probe 101, and acquires the shape of the probe 101 inside the subject 900 from the magnetic fields generated from the source coils.

Sixth Modification

In the above described first embodiment, the source coil 102a is provided in the end portion 102 of the probe 101, and the magnetic field FS generated spontaneously from the source coil 102a by inputting a sinusoidal signal to the source coil 102a is detected. From the detection results (detection signals), the location of the source coil 102a (or the end portion 102) is calculated. This is a so-called active location detection method. However, the present invention is not limited to that, and it is of course possible to utilize a so-called passive location detection method. According to the passive location detection method, an LC resonant circuit is provided in the end portion 102, and a resonant magnetic field generated by applying an external magnetic field at a predetermined resonant frequency to the LC resonant circuit is detected. From the detection results (detection signals), the location of the LC resonant circuit (or the end portion 102) is calculated.

Likewise, in the above described second embodiment, the antenna 25a having directionality is provided in the capsule endoscope 20, and the field distribution formed by the antenna 25a when image data is transmitted is detected. From the results of this detection, the location of the antenna 25a (or the capsule endoscope 20) is calculated. However, the present invention is not limited to that location detection method, and it is of course possible to utilize a passive location detection method or a so-called three-dimensional measurement method. According to the passive location detection method, an LC resonant circuit is provided in the capsule endoscope 20, and the resonant magnetic field generated by applying an external magnetic field at a predetermined resonant frequency to the LC resonant circuit is detected. From the detection results (detection signals), the location of the LC resonant circuit (or the capsule endoscope 20) is calculated. According to the three-dimensional measurement method, the location information about the capsule endoscope 20 is calculated from the radio field intensities of radio signals received by the plurality of antennas A from the capsule endoscope 20.

Further, in the above described third embodiment, the LC resonant circuit 31 is provided in the capsule endoscope 30, and the resonant magnetic field generated by applying an external magnetic field at a predetermined resonant frequency to the LC resonant circuit 31 is detected. From the detection results (detection signals), the location of the LC resonant circuit 31 (or the capsule endoscope 20) is calculated. This is a passive location detection method. However, the present invention is not limited to that, and it is of course possible to utilize an active location detection method. According to the active location detection method, the same source coil 102a as that of the above described first embodiment is provided in the capsule endoscope 20, for example, and the magnetic field generated spontaneously from the source coil 102a by inputting a sinusoidal signal at a predetermined frequency to the source coil 102a is detected. From the detection results (detection signals), the location of the source coil (or the capsule endoscope 20) is calculated.

The above described embodiments (including the modifications) are merely examples for carrying out the present invention, and the present invention is not limited to them.

Various modifications made depending on specifications and the like are within the scope of the present invention, and it is obvious from the above disclosure that various other embodiments can be formed.

According to the embodiments described so far, the first movement trajectory currently acquired can be adjusted to the existing second movement trajectory. Accordingly, it is possible to realize an in-vivo examination system that enables an observer to accurately identify observed regions, regardless of the knowledge, experience, and expertise of the observer, by linking predetermined locations on the existing second movement trajectory with relevant information about the observed regions, for example.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo examination system comprising:
a body-insertable apparatus that moves in a subject; and
an external device that acquires information about an inside of the subject from the body-insertable apparatus,
the external device including
a location acquiring unit that acquires a plurality of first locations of the body-insertable apparatus in the subject;
a trajectory generating unit that generates a first movement trajectory of the body-insertable apparatus in the subject, based on the plurality of first locations, by connecting a plurality of sequential points;
a trajectory storage unit that stores a second movement trajectory that is a standard movement trajectory that is obtained when the body-insertable apparatus moves in a standard subject, the second movement trajectory being generated by connecting a plurality of sequential points, the second movement trajectory being defined by a line formed by copying a lumen of a standard subject previously stored and connecting center points of the lumen;
a scale adjusting unit that adjusts the first movement trajectory to the second movement trajectory by partially and/or entirely reducing or enlarging a scale of the first movement trajectory so that a current location on a movement trajectory being currently acquired in the first movement trajectory is acquired as a current location on the second movement trajectory;
a trajectory image generating unit that generates an image of the second movement trajectory;
an average color bar generating unit that acquires image data from the body-insertable apparatus, calculates an average color of the acquired image data in each set of the image data, generates a hue image that visually represents the hues of each set of image data in one color, based on the calculated average color, and generates an average color bar image by combining the generated hue images in chronological order;
a display unit that displays a current location of the body-insertable apparatus acquired by the location acquiring unit, the current location being superimposed on an image of the second movement trajectory, and displays the image of the second movement trajectory together with the average color bar image; and
a relevant information storage unit that stores relevant information associated with one or more second locations set on the second movement trajectory,
wherein the relevant information contains average colors at the second locations with which the relevant information is associated,
the calculated average color is compared with a value of an average color that stored as the relevant information in the relevant information storage unit, and
a notification is made based on the comparison result.

* * * * *